(12) United States Patent
Budhlall et al.

(10) Patent No.: US 9,163,114 B2
(45) Date of Patent: Oct. 20, 2015

(54) BIODEGRADABLE SHAPE MEMORY POLYMER

(75) Inventors: Bridgette M. Budhlall, Dracut, MA (US); Amit L. Garle, New Haven, CT (US)

(73) Assignee: University of Massachusetts, Boston, MA (US)

(*) Notice: Subject to any disclaimer, the term of this patent is extended or adjusted under 35 U.S.C. 154(b) by 59 days.

(21) Appl. No.: 13/818,408

(22) PCT Filed: Aug. 25, 2011

(86) PCT No.: PCT/US2011/049152
§ 371 (c)(1),
(2), (4) Date: Feb. 22, 2013

(87) PCT Pub. No.: WO2012/027573
PCT Pub. Date: Mar. 1, 2012

(65) Prior Publication Data
US 2013/0150533 A1 Jun. 13, 2013

Related U.S. Application Data

(60) Provisional application No. 61/376,968, filed on Aug. 25, 2010.

(51) Int. Cl.
*C08G 6/00* (2006.01)
*C08G 63/672* (2006.01)
(Continued)

(52) U.S. Cl.
CPC ............ *C08G 63/672* (2013.01); *C07D 267/10* (2013.01); *C07D 313/04* (2013.01);
(Continued)

(58) Field of Classification Search
CPC .................................................... C08G 63/672
USPC ............. 528/220, 80, 76, 176, 271, 272, 193, 528/196, 301; 525/447; 549/271, 266, 267, 549/10, 11; 540/544
See application file for complete search history.

(56) References Cited

U.S. PATENT DOCUMENTS 4,833,259 A 5/1989 Erlemann et al.
6,160,084 A 12/2000 Langer et al.
(Continued)

FOREIGN PATENT DOCUMENTS

WO WO 98/22454 A1 5/1998
WO WO 2006/123762 A1 11/2006
WO WO 2012/027573 A2 3/2012

OTHER PUBLICATIONS

Allan, R. D., et al., "A New Synthesis, Resolution and in Vitro Activities of (R)- and (S)-β-phenyl-GABA," Tetrahedron, 46(7): 2511-2524 (1990).
(Continued)

*Primary Examiner* — Duc Truong
(74) *Attorney, Agent, or Firm* — Hamilton, Brook, Smith & Reynolds, P.C.

(57) ABSTRACT

A shape-memory polymers comprising at least one monomer subunit represented by the following structural formula (1).

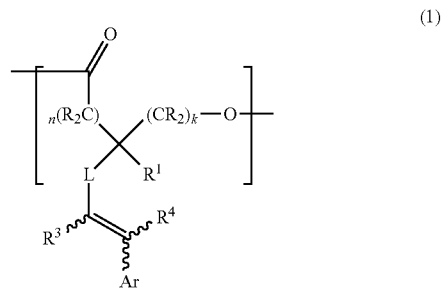

39 Claims, 5 Drawing Sheets

(51) Int. Cl.
C07D 313/04 (2006.01)
C07D 267/10 (2006.01)
C07D 323/00 (2006.01)
C07D 327/00 (2006.01)
C07D 327/02 (2006.01)
C08G 65/332 (2006.01)
C08G 63/08 (2006.01)

(52) U.S. Cl.
CPC ............ C07D323/00 (2013.01); C07D 327/00 (2013.01); C07D 327/02 (2013.01); C08G 63/08 (2013.01); C08G 65/3324 (2013.01)

(56) References Cited

U.S. PATENT DOCUMENTS

| | | | |
|---|---|---|---|
| 6,388,043 | B1 | 5/2002 | Langer et al. |
| 6,720,402 | B2 | 4/2004 | Langer et al. |
| 2006/0036045 | A1 | 2/2006 | Wilson et al. |
| 2006/0287710 | A1 | 12/2006 | Lendlein et al. |
| 2008/0177303 | A1 | 7/2008 | Anthamatten et al. |
| 2009/0131557 | A1 | 5/2009 | Uyama et al. |

OTHER PUBLICATIONS

Feng, Y., et al., "Biodegradable Multiblock Copolymers Based on Oligodepsipeptides with Shape-Memory Properties," *Macromol. Biosci.*, 9: 45-54 (2009).

Garle, A., et al., "Combination of ROP and RAFT for synthesis of a novel biodegradable, stimuli responsive P(CL-*ran*-CCL)-b-PNIPAm-*b*-P(CL-*ran*-CCL) triblock copolymer," *PMSE Preprints*, 101: 1221-1222 (2009).

Garle, A., et al., "Design and Synthesis of a Novel Biodegradable Polymer for Biomedical Applications," *Polymer Preprints—America—CD-ROM Edition*, 51(2): 254-255 (2010).

Garle, A., and Kong, S., "Synthesis and Shape memory characterization of a Novel Polyester for Potential Biomedical applications," ACS talk sent to CVIP (Jul. 16, 2010).

Hu, X., et al., "Cinnamate-Functionalized Poly(ester-carbonate): Synthesis and Its UV Irradiation-Induced Photo-Crosslinking," *Journal of Polymer Science: Part A: Polymer Chemistry*, 47: 161-169 (2009).

Lee, K. M., et al., "Polycaprolactone-POSS Chemical/Physical Double Networks," *Macromolecules*, 41(13): 4730-4738 (2008).

Lendlein, A., and Langer, R., "Biodegradable, Elastic Shape-Memory Polymers for Potential Biomedical Applications," *Science*, 296: 1673-1676 (2002).

mNEMOSCIENCE, "Products—In-house Programs—Surgical Sutures," at least as early as Aug. 2010.

Nagahama, K., et al., "Biodegradable Shape-Memory Polymers Exhibiting Sharp Thermal Transitions and Controlled Drug Release," *Biomacromolecules*, 10: 1789-1794 (2009).

Nagata, M., and Sato, Y., "Synthesis and Properties of Photocurable Biodegradable Multiblock Copolymers Based on Poly($\epsilon$-caprolactone) and Poly(L-lactide) Segments," *Journal of Polymer Science: Part A: Polymer Chemistry*, 43: 2426-2439 (2005).

Nagata, M., and Yamamoto, Y., "Photocurable Shape-Memory Copolymers of $\epsilon$-Caprolactone and L-Lactide," *Macromol. Chem. Phys.*, 211(16):1826-1835 (Aug. 2010).

Nagata, M., and Yamamoto, Y., "Synthesis and Characterization of Photocrosslinked Poly($\epsilon$-caprolactone)s Showing Shape-Memory Properties," *Journal of Polymer Science: Part A: Polymer Chemistry*, 47: 2422-2433 (2009).

Sung, S.-J., et al., "Poly($\epsilon$-caprolactone) diol functionalized with a cinnamoyl group and its UV-triggered in-plane alignment," *Reactive & Functional Polymers*, 70: 622-629 (2010).

Wanamaker, C. L., et al., "Renewable-Resource Thermoplastic Elastomers Based on Polylactide and Polymenthide," *Biomacromolecules*, 8: 3634-3640 (2007).

Yoshida, M., et al., "From Advanced Biomedical Coatings to Multi-Functionalized Biomaterials," *Polymer Reviews*, 46: 347-375 (2006).

International Search Report and Written Opinion of the International Searching Authority from International Application No. PCT/US2011/049152, "Biodegradable Shape Memory Polymer,", mailed on Apr. 30, 2012.

BIODEGRADABLE SHAPE MEMORY POLYMER

RELATED APPLICATIONS

This application is the U.S. National Stage of International Application No. PCT/US2011/049152, filed Aug. 25, 2011, which designates the U.S., published in English, and claims the benefit of U.S. Provisional Application No. 61/376,968 filed on Aug. 25, 2010. The entire teachings of the above applications are incorporated herein by reference.

GOVERNMENT SUPPORT

This invention was made with government support under NSF-0425826 awarded by the National Science Foundation. The government has certain rights in the invention.

BACKGROUND OF THE INVENTION

Shape memory alloys, such as TiNi alloys, have been applied widely in medical fields (e.g. as a urethra arterial stent for enlarged prostate) due to their unique shape memory effect, high strength and excellent biocompatibility. However, these alloys show some obvious disadvantages, such as high manufacturing cost, limited recoverable deformation and lack of biodegradability.

Recently, biodegradable shape-memory polymers (SMPs) have attracted much attention and several kinds of biodegradable polymers have been reported. Specifically, SMPs can be produced from different natural or synthetic raw polymers, such as chitosan, cellulose, polyetherurethanes, poly($\epsilon$-caprolactone). The synthesis and post treatment methods of the polymers were complicated and the mechanical properties are insufficient for various biomedical applications.

SUMMARY OF THE INVENTION

A great need exists to develop a shape memory polymer with improved combination of properties: tunable thermal, mechanical, biodegradation properties, with better processibility, better biocompatibility, lower modulus near the elastic modulus of human tissue and faster controlled release profiles.

In one embodiment, the present invention is a chemical compound of the following structural formula:

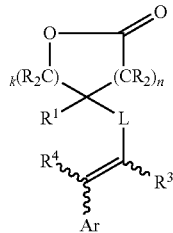

(I)

In formula (I), Ar is an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group; k and n are each independently zero or an integer between 1 and 6, provided that k+n≤14; L is selected from —X—, —N(R$^2$)—, —C(X)—, —C(X)X—, —XC(X)—, —C(X)NR$^2$—, —NR$^2$C(X)—, —N(R$^2$)—S(O)$_m$—, —S(O)$_m$—N(R$^2$)—; each X is independently an O or an S; m is 1 or 2; and R, R$^1$, R$^2$, R$^3$ and R$^4$ for each occurrence is each independently selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkynyl group, C1-C12 alkoxy, or C1-C12 haloalkyl.

In another embodiment, the present invention is a polymer comprising at least one repeat unit represented by the following structural formula:

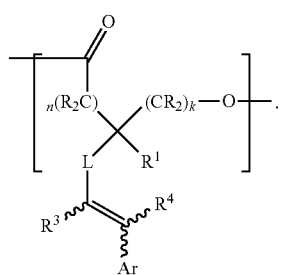

(III)

Values and preferred values of the variables in structural formula (III) are as defined with respect to structural formula (I).

In another embodiment, the present invention is a method of cross-linking a polymer. The method comprises irradiating a starting polymer comprising at least one repeat unit of structural formula (III) with actinic radiation

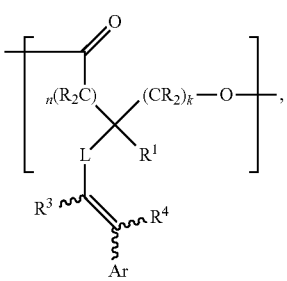

(III)

thereby producing a polymer having at least two cross-linked repeat units represented by structural formulas (VIII) or (VIIIA):
thereby producing a polymer having at least two cross-linked repeat units represented by structural formulas (VIII) or (VIIIA)

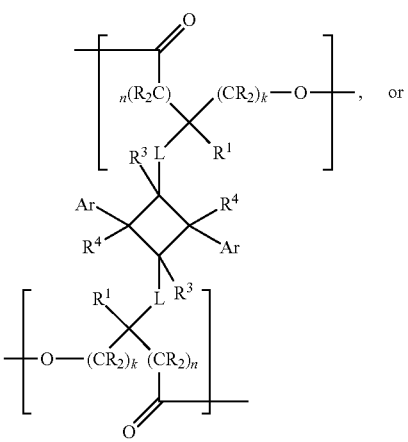

(VIII)

-continued

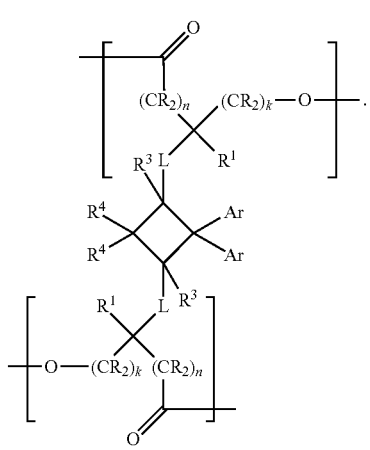
(VIIIA)

Values and preferred values of the variables in structural formulas (VIII) or (VIIIA) are as defined with respect to structural formula (III).

In another embodiment, the present invention is a method of synthesis of a polymer having at least one subunit represented by the following structural formula

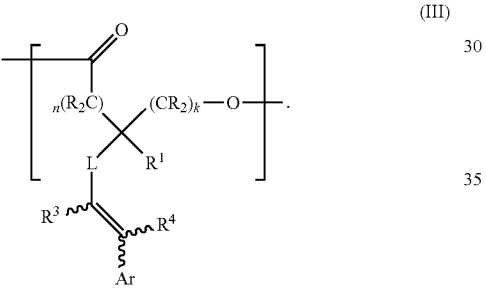
(III)

The method comprises reacting a compound of structural formula (I)

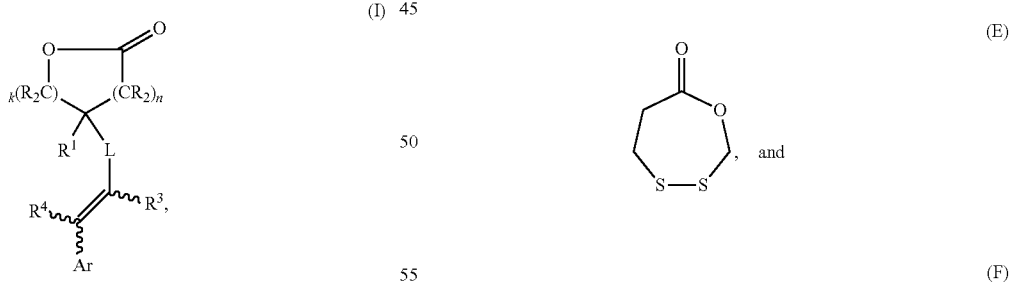
(I)

with a compound of structural formula (VII)

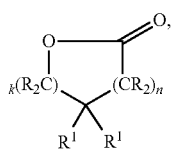
(VII)

thereby producing the polymer having at least one subunit of structural formula (III). Values and preferred values of the variables in structural formula (VII) are as defined with respect to structural formula (I).

In another embodiment, the present invention is a chemical compound represented by a structural formula selected from the group consisting of:

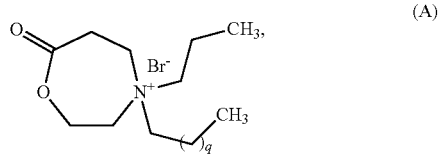
(A)

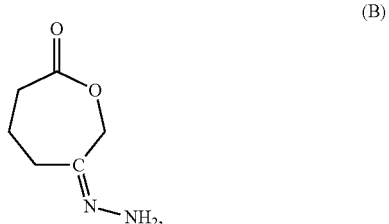
(B)

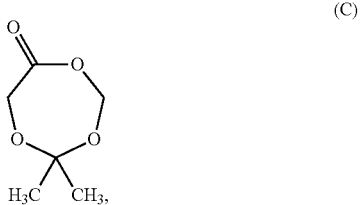
(C)

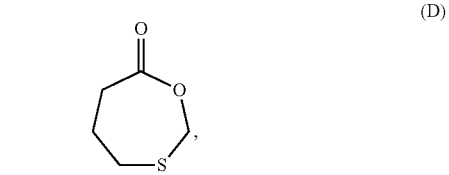
(D)

(E)

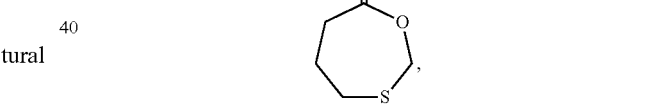

(F)

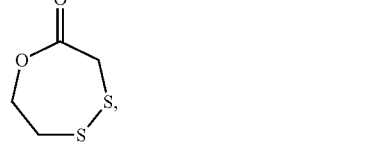

wherein q is an integer from 1 to 10.

In another embodiment, the present invention is a polymer comprising at least one repeat unit represented by the following structural formula:

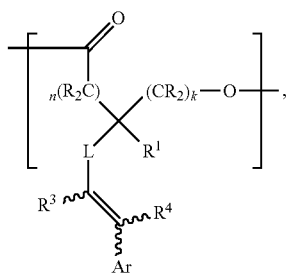

and at least one repeat unit represented by the structural formula selected from the group consisting of:

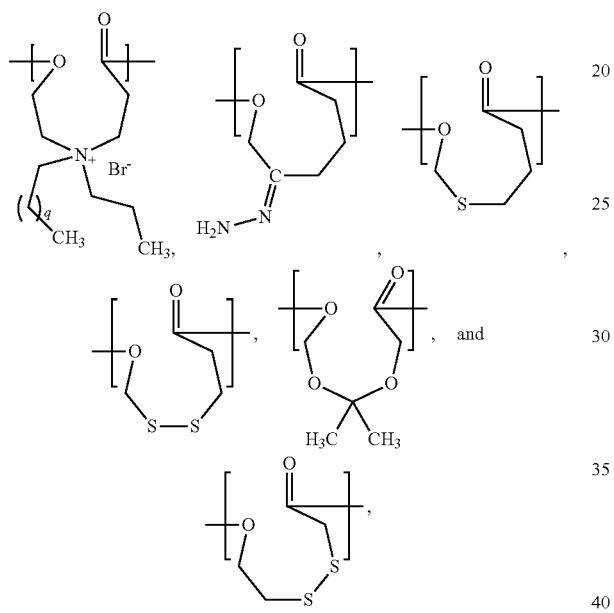

wherein q is an integer from 1 to 10. Values and preferred values of the variables in the above structural formulas are as defined with respect to structural formula (I).

In another embodiment, the present invention is a method of cross-linking a polymer. The method comprises irradiating a starting polymer comprising at least one repeat unit of structural formula (III) with actinic radiation

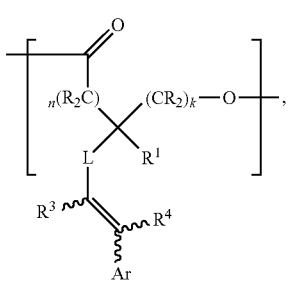

thereby producing a polymer having at least two cross-linked repeat units represented by structural formulas (VIII) or (VIIIa)

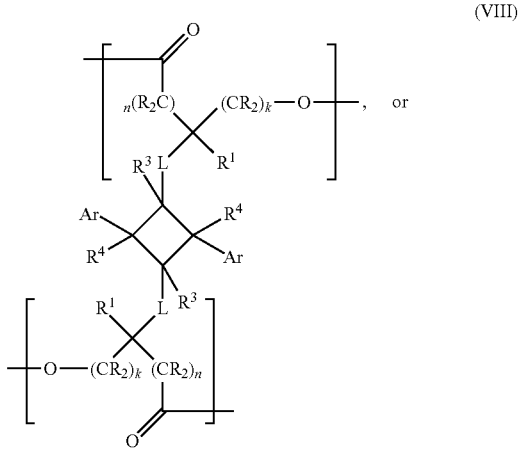

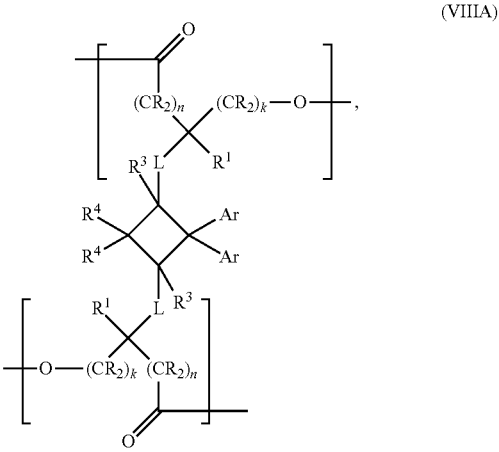

wherein the starting polymer further comprises at least one repeat unit represented by the structural formula selected from the group consisting of:

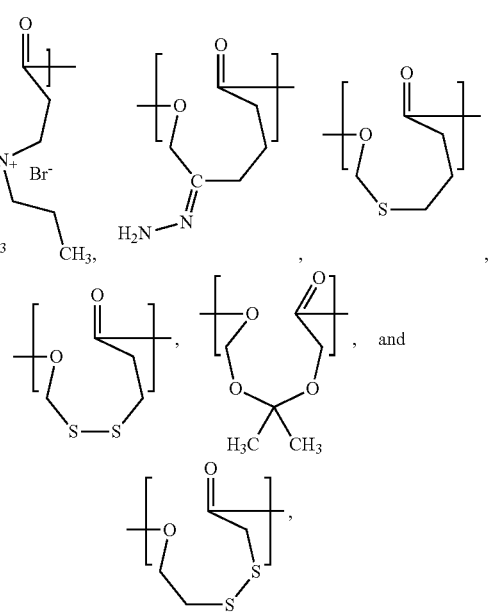

wherein q is an integer from 1 to 10. Values and preferred values of the variables in the above structural formulas are as defined with respect to structural formula (I).

In another embodiment, the present invention is a method of synthesis of a polymer having at least one subunit represented by the following structural formula

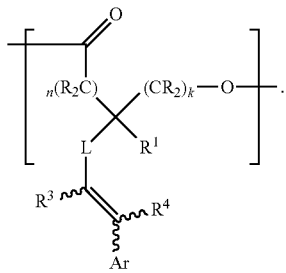
(III)

The method comprises reacting a compound of structural formula (I)

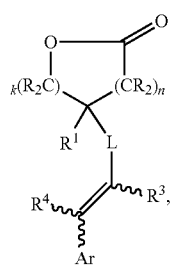
(I)

with at least one compound represented by a structural formula selected from the group consisting of:

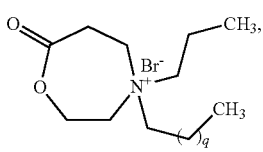
(A)

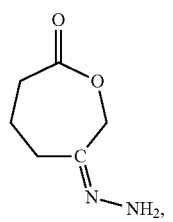
(B)

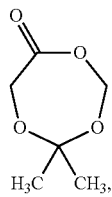
(C)

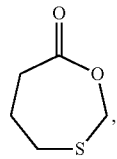
(D)

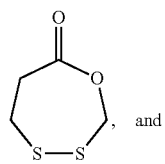
(E)
, and

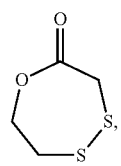
(F)

wherein q is an integer from 1 to 10, thereby producing the polymer having at least one subunit of structural formula (III). Values and preferred values of the variables in the above structural formulas are as defined with respect to structural formula (I).

The (co)polymers of the present invention can be used to manufacture a wide variety of deployable structures with complex shape. For example, the (co)polymers of the present invention can be used to manufacture medical devices such as stents, catheters, sutures, prosthetics, grafts, screws, pins, plates, pumps, meshes and wound dressings, or eyeglasses. Alternatively, the (co)polymers of the present invention can be used to manufacture an optical shutter for thermal sensing, reversible embossing for information storage or for microfluidic devices, or an adhesive comprising a shape memory composition. The (co)polymers of the present invention can be used to manufacture can be cast, extruded or molded in the shape a film, coating or as a solid casting. The (co)polymers of the present invention can further include dyes.

The (co)polymers described herein provides important advantages. The switching temperature and mechanical properties of tri-block copolymers of ε-caprolactone or its derivatives or analogs can be controlled by controlling the molecular weight of the polycaprolactone blocks. Antimicrobial functionalities can be incorporated into the (co)polymer by using, e.g., monomer A. (Co)polymers that incorporate monomer A can be used in medical devices, drug delivery vehicles, and health care and hygienic applications, water purification systems, hospital and dental surgery equipment, textiles, food packaging, and food storage, among other applications. Biodegradation rates of (co)polymers can be controlled by incorporating monomers B, C, D, E or F, depending on the degradation stimuli and rate desired. (Co) polymers that incorporate monomers B and C can be used for drug eluting bioimplants (or drug delivery vehicles), especially for delivery of pharmaceutically active ingredients of to the acidic environments of tumors, inflammatory tissues, and phagosomes.

DETAILED DESCRIPTION OF THE INVENTION

Definitions of Terms

Figure 1:
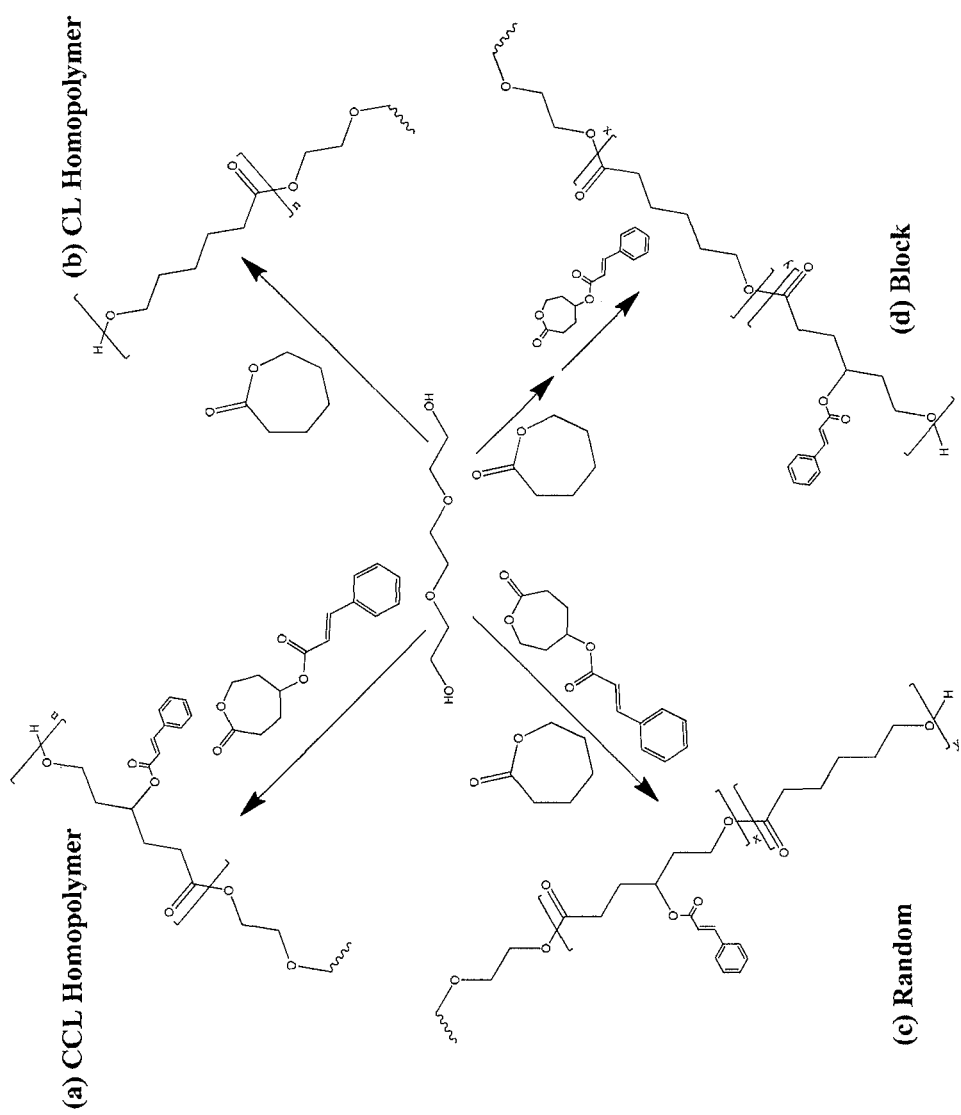
FIG. 1 is a schematic diagram of various synthetic schemes that employ the chemical compounds of the present invention.

The term "alkyl", as used herein, unless otherwise indicated, means straight or branched saturated monovalent hydrocarbon radicals of formula $C_nH_{2n+1}$. In some embodiments, n is from 1 to 18. In other embodiments, n is from 1 to 12. Preferably, n is from 1 to 6. In some embodiments, n is 1-1000, for example, n is 1-100. Alkyl can optionally be substituted with —OH, —SH, halogen, amino, cyano, nitro, a C1-C12 alkyl, C1-C12 haloalkyl, C1-C12 alkoxy, C1-C12 haloalkoxy or C1-C12 alkyl sulfanyl. In some embodiments, alkyl can optionally be substituted with one or more halogen, hydroxyl, C1-C12 alkyl, C2-C12 alkenyl or C2-C12 alkynyl group, C1-C12 alkoxy, or C1-C12 haloalkyl. The term alkyl can also refer to cycloalkyl.

As used herein, an "alkenyl group", alone or as a part of a larger moiety (e.g., cycloalkene oxide), is preferably a straight chained or branched aliphatic group having one or more double bonds with 2 to about 12 carbon atoms, e.g., ethenyl, 1-propenyl, 1-butenyl, 2-butenyl, 2-methyl-1-propenyl, pentenyl, hexenyl, heptenyl or octenyl, or a cycloaliphatic group having one or more double bonds with 3 to about 12 carbon atoms.

As used herein, an "alkynyl" group, alone or as a part of a larger moiety, is preferably a straight chained or branched aliphatic group having one or more triple bonds with 2 to about 12 carbon atoms, e.g., ethynyl, 1-propynyl, 1-butynyl, 3-methyl-1-butynyl, 3,3-dimethyl-1-butynyl, pentynyl, hexynyl, heptynyl or octynyl, or a cycloaliphatic group having one or more triple bonds with 3 to about 12 carbon atoms.

The term "cycloalkyl", as used herein, means saturated cyclic hydrocarbons, i.e. compounds where all ring atoms are carbons. In some embodiments, a cycloalkyl comprises from 3 to 18 carbons. Preferably, a cycloalkyl comprises from 3 to 6 carbons. Examples of cycloalkyl include, but are not limited to, cyclopropyl, cyclobutyl, cyclopentyl, cyclohexyl, and cycloheptyl. In some embodiments, cycloalkyl can optionally be substituted with one or more halogen, hydroxyl, C1-C12 alkyl, C2-C12 alkenyl or C2-C12 alkynyl group, C1-C12 alkoxy, or C1-C12 haloalkyl.

The term "haloalkyl", as used herein, includes an alkyl substituted with one or more F, Cl, Br, or I, wherein alkyl is defined above.

The terms "alkoxy," as used herein, means an "alkyl-O—" group, wherein alkyl is defined above. Examples of alkoxy group include methoxy or ethoxy groups.

The term "aryl," as used herein, refers to a carbocyclic.aromatic group. Preferably, an aryl comprises from 6 to 18 carbons. Examples of aryl groups include, but are not limited to phenyl and naphthyl. Examples of aryl groups include optionally substituted groups such as phenyl, biphenyl, naphthyl, phenanthryl, anthracenyl, pyrenyl, fluoranthyl or fluorenyl. An aryl can be optionally substituted. Examples of suitable substituents on an aryl include halogen, hydroxyl, C1-C12 alkyl, C2-C12 alkene or C2-C12 alkyne, C3-C12 cycloalkyl, C1-C12 haloalkyl, C1-C12 alkoxy, aryloxy, arylamino or aryl group.

In some embodiments, a C6-C18 aryl selected from the group consisting of phenyl, indenyl, naphthyl, azulenyl, heptalenyl, biphenyl, indacenyl, acenaphthylenyl, fluorenyl, phenalenyl, phenanthrenyl, anthracenyl, cyclopentacyclooctenyl or benzocyclooctenyl. In some embodiments, a C6-C14 aryl selected from the group consisting of phenyl, naphthalene, anthracene, 1H-phenalene, tetracene, and pentacene.

The term "aryloxy," as used herein, means an "aryl-O—" group, wherein aryl is defined above. Examples of an aryloxy group include phenoxy or naphthoxy groups.

The term (hetero)arylamine, as used herein, means an "(hetero)aryl-NH—", an "(hetero)aryl-N(alkyl)-", or an "((hetero)aryl)$_2$-N-" groups, wherein (hetero)aryl and alkyl are defined above.

The term "heteroaryl," as used herein, refers to aromatic groups containing one or more heteroatoms (O, S, or N). A heteroaryl group can be monocyclic or polycyclic, e.g. a monocyclic heteroaryl ring fused to one or more carbocyclic aromatic groups or other monocyclic heteroaryl groups. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

In other embodiments, a 5-14-membered heteroaryl group selected from the group consisting of pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl.

The foregoing heteroaryl groups may be C-attached or N-attached (where such is possible). For instance, a group derived from pyrrole may be pyrrol-1-yl (N-attached) or pyrrol-3-yl (C-attached).

Suitable substituents for heteroaryl are as defined above with respect to aryl group.

Suitable substituents for an alkyl, cycloalkyl include a halogen, an alkyl, an alkenyl, a cycloalkyl, a cycloalkenyl, an aryl, a heteroaryl, a haloalkyl, cyano, nitro, haloalkoxy.

Further examples of suitable substituents for a substitutable carbon atom in an aryl, a heteroaryl, alkyl or cycloalkyl include but are not limited to —OH, halogen (—F, —Cl, —Br, and —I), —R, —OR, —CH$_2$R, —CH$_2$OR, —CH$_2$CH$_2$OR. Each R is independently an alkyl group.

In some embodiments, suitable substituents for a substitutable carbon atom in an aryl, a heteroaryl or an aryl portion of an arylalkenyl include halogen, hydroxyl, C1-C12 alkyl, C2-C12 alkenyl or C2-C12 alkynyl group, C1-C12 alkoxy, aryloxy group, arylamino group and C1-C12 haloalkyl.

In addition, the above-mentioned groups may also be substituted with =O, =S, =N-alkyl.

In the context of the present invention, an amino group may be a primary (—NH$_2$), secondary (—NHR$_p$), or tertiary (—NR$_p$R$_q$), wherein R$_p$ and R$_q$ may be any of the alkyl, alkenyl, alkynyl, alkoxy, cycloalkyl, cycloalkoxy, aryl, heteroaryl, and a bicyclic carbocyclic group. A (di)alkylamino group is an instance of an amino group substituted with one or two alkyls.

A "trialkylamino" group is a group —N$^+$(R$_t$)$_3$, wherein R$_t$ is an alkyl, as defined above.

The terms "MCL" and "CCL" are used interchangeably and both refer to cinnamoyl-caprolactone.

Shape-Memory Polymers

In various embodiments, the present invention is a novel chemical compound, a polymer comprising same and methods for manufacturing same. Advantageously, the compounds and polymers of the present invention can be employed in shape-memory polymers.

"Shape-memory polymers" are polymers, which have a special chemical makeup that gives them a shape-memory effect. The polymer is produced initially in its permanent shape. The temporary shape is imparted under strain followed by physical crosslinking or chemical crosslinking. On cooling below the transition temperature, the temporary shape is retained. Heating the polymer up to above its so-called "switching temperature" T$_{switch}$, the permanent shape is recovered. The switch temperature or transition temperature can be glass transition temperature or melting transition temperature.

At a temperature below T$_{switch}$ the shape memory polymer, now in its temporary shape, can be stored until its use. This transition from the original to temporary shapes can be repeated over and over again without the polymer degrading. Depending on the chemical composition, the transition temperature of a shape-memory polymer can be varied, and may be as low as −30 degrees Celsius and could go up to 260 degrees Celsius.

A polymer of the present invention possesses the ability for shape memory dimensional changes. Such a polymer can be used, for example, to manufacture a medical device that is small when implanted in the body, but later self-expands or changes its flexibility, thus adjusting to anatomical structures. Shape memory can be achieved in several ways. For example, incorporation of UV active functional groups in the main chain of a copolymer can permit modification of the modulus (a measure of rigidity or flexibility) of the copolymer by UV crosslinking.

Alternatively, the use of a monomer with a low melting point (T$_m$=52° C.), for example ε-caprolactone, can enable the polymer to transition from one shape to another using a temperature that is near physiological conditions. Further advantage of a polymer of the present invention is its biodegradability and biocompatibility, enabling its use in in-vivo applications. In the case of a coronary stent, for example, this would ensure that after the stent has widened the artery, it will biodegrade at a pre-programmed degradation rate between 6 and 24 months, depending on the surgical demands on the stent.

In one embodiment, the present invention is a biodegradable shape memory polymer with dual shape memory and dual stimuli-response. The choice of monomers is based on their known biocompatibility, biodegradability, and glass transition and melting temperatures.

The shape-memory effect can be triggered by reversible UV crosslinking and/or heat and can be exploited after specific processing referred to as "programming." For UV activated shape memory polymer, the polymer is produced initially in its permanent shape, subjected to strain followed by exposure of UV light (e.g. by exposure to light of wavelength greater than 260 nm) to induce chemical crosslinking (e.g., of the vinyl groups in the modified caprolactone), resulting in a desired temporary shape. On exposure to UV light, the polymer returns back to its permanent shape.

At a temperature below T$_{switch}$ the shape-memory polymer (SMP), now in its temporary shape, can be stored until its use. In the embodiments employing ε-caprolactone as one of the blocks in the copolymer, one transition, T$_{switch}$ can be the melting point of poly(ε-caprolactone) (T$_m$=52° C.) and the other transition can be reversible crosslinking. The crosslinking can be conducted with UV curable vinyl groups grafted along the length of the end blocks.

One example of a suitable polymer is a (co)polymer, in some embodiments—derivatives, of polycaprolactone (PCL). PCL is biodegradable polyester with a low melting point of around 52° C. and a glass transition temperature of about −60° C. PCL is degraded by hydrolysis of its ester linkages in physiological conditions (such as in the human body) and has therefore received a great deal of attention for use as an implantable biomaterial. In the body, heating can be achieved by incorporating metallic nanoparticles that can absorb near infra-red radiation or be inductively heated by a magnetic field. Incorporating these nanoparticles will enable shape memory actuation inside the body using temperature as the switch. Radiation in controlled doses can be used for in-vivo imaging because of minimal light absorption by hemoglobin (>650 nm) and water (<900 nm). Radiation between 650 nm and 900 nm can thus be safely used to heat the polymer matrix. Alternatively, magnetic nanoparticles can be homogeneously incorporated in the shape-memory polymer matrix. The shape-memory effect of the nanoparticle/polymer composite systems could be induced by inductive heating in an alternating magnetic field (for example, f=258 kHz; H=30 kA·m$^{-1}$). The maximum temperatures achievable by inductive heating in a specific magnetic field will depend on sample geometry and nanoparticle content. The inductive heating of the nanoparticles will generate heat locally within the polymer.

Thermoplastic elastomers based on biodegradable polymers such as poly(lactide), poly(glycolide) and poly(ε-caprolactone) posses great potential for biomedical applications. The crystallinity of these polymers is critical for various properties such as degradability, shape memory behavior and mechanical properties such as tensile strength, ultimate elongation, etc. Crystallinity in polymers can act as a crosslinking mechanism greatly affecting its properties. Variation of crystallinity can be achieved by chemical modification of the polymer backbone in a controlled manner and by different polymer architectures. ε-Caprolactone is a semicrystalline polymer with a high degree of crystallinity. Modifying e-caprolactone monomer with a functional group which can be crosslinked by UV and polymerized in a controlled manner can affect the crystallinity to enhance the mechanical properties and tensile strength of copolymers based on poly(ε-caprolactone), enabling their use in biomedical applications. For example, modifying poly(lactide) with cyclopentadiene to synthesize a binary blend of poly(lactide) and poly(1,5-cyclopentadiene) has been accomplished. Cross linking with UV radiation is also useful for biomedical applications as it does not involve any initiator or crosslinker which can remain in the polymer and leach out during degradation of poly(ε-caprolactone).

Accordingly, in one embodiment, the present invention is a shape memory polymer composition obtained by copolymerizing a first and a second monomer. Preferably, the homopolymers formed by the first and the second monomers have different glass transition temperatures. The resulting copolymer preferably has a glass transition temperature between the glass transition temperatures of the two homopolymers. Preferably, the glass transition temperature of the resulting copolymer is from −75-110° C. In some embodiments, a multifunctional monomer is incorporated into the copolymerization reaction mixture. Preferably, the multifunctional monomer is a difunctional monomer.

In some embodiments, the present invention is a method of forming a shape-memory composition. The method comprises the step of preparing a copolymer comprising a first monomer and a second monomer. The homopolymers of each of the first and the second monomers have different glass transition temperatures. Preferably, the first and the second monomers are copolymerized in the presence of a multifunctional, preferably difunctional, monomer. Preferably, the multifunctional monomer crosslinks the copolymer chains. Preferably, the resulting cross-linked copolymer has a glass transition temperature between glass transition temperatures of the homopolymers formed from the first and the second monomers. The method further comprises shaping a composition to an original shape while heating said composition to form a temporary shape and quenching the temporary shape in temperatures below the melting temperature of the copolymer (Tm). The method further comprises heating the quenched sample at temperatures above Tm whereby the temporary shape is returned to the original shape.

In various embodiments, the copolymers of the present invention are random or ordered block copolymers that include subunits of structural formulas of the monomers defined below. For example, the copolymer can be a triblock copolymer of general formula $(A)_x(B)_y(A)_z$, where "A" and "B" represent the monomers disclosed herein, and x, y and z are each independently an integer. For example, structural "A" can represent a monomer of structural formula (IV) and "B" can represent a subunit of structural formula (III). Each A can be the same of different. Similarly, each B can be the same of different. Alternatively, the copolymer can be a random copolymer of general formula $(A)_w(B)_v$ where w and v are each independently an integer. In other embodiments, the copolymer can be a copolymer of general formula $(AB)_u$, where u is an integer.

Monomers and Polymers of the Invention

In the chemical formulas reproduced below, the symbol "〜〜〜" means that no specific E or Z configuration around the double bond in question is specified.

In one embodiment, the present invention is a chemical compound of the following structural formula:

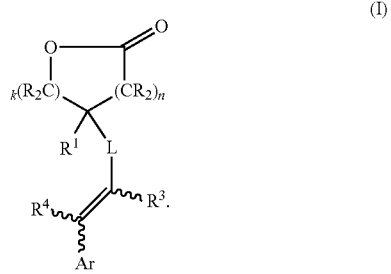

(I)

In structural formula (I), Ar is an aryl or a heteroaryl, k and n are each independently zero or an integer from 1 to 14; L is selected from —X—, —N(R²)—, —C(X)—, —C(X)X—, —XC(X)—, —C(X)NR²—, —NR²C(X)—, —N(R²)—S(O)$_m$—, —S(O)$_m$—N(R²)—, where each X is independently an O or an S; and m is 1 or 2. R, R¹, R², R³ and R⁴ for each occurrence is each independently selected from hydrogen, an alkyl, alkenyl, an alkyne, or a (hetero)aryl group.

In another embodiment, the present invention is a chemical compound of structural formula (I), wherein L is selected from —X—, —N(R²)—, —C(X)—, —C(X)X—, —XC(X)—, —C(X)NR²—, —NR²C(X)—. The values and preferred values of the remainder of the variables are as defined above with respect to formula (I).

In another embodiment, the present invention is a chemical compound of structural formula (I), wherein Ar is an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group. Preferably, Ar is an aryl, more preferably Ar is a C6-C18 aryl. More preferably, Ar is phenyl. The values and preferred values of the remainder of the variables are as defined above with respect to formula (I).

In another embodiment, the present invention is a chemical compound of structural formula (I), wherein k and n are each independently zero or an integer between 1 and 6, provided that k+n≤14. Preferably, k and n each independently is selected from zero or an integer from 1 to 3. More preferably, k and n are each independently selected from 0, 1, 2 or 3. In some examples, each n and k are equal to 2. In other examples, k and n are each independently selected from 0, 1 and 2. The values and preferred values of the remainder of the variables are as defined above with respect to formula (I).

In another embodiment, the present invention is a chemical compound of structural formula (I), wherein R, R¹, R², R³ and R⁴ for each occurrence is each independently selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkynyl group, C1-C12 alkoxy, or C1-C12 haloalkyl. Preferably, R, R¹, R², R³ and R⁴ for each occurrence is independently selected from a hydrogen, a C1-C12 alkyl, a C3-C12 cycloalkyl, a C2-C12 alkenyl, a C3-C12 cycloalkenyl, a C3-C12 cycloalkynyl, a C2-C12 alkynyl, a (C6-C18)aryl(C6-C12)alkyl, or a (C6-C18)heteroaryl(C6-C12)alkyl. More preferably R¹, R², R³ and R⁴ each is hydrogen, while the values and preferred values of R are defined above with respect to formula (I). Even more preferably, R for each occurrence is independently selected from a hydrogen, a C1-C12 alkyl, a C3-C12 cycloalkyl, a C2-C12 alkenyl, a (C6-C18)aryl(C6-C12)alkyl, or a (C6-C18)heteroaryl(C6-C12)alkyl, while the values and preferred values of R¹, R², R³ and R⁴ are as defined above with respect to formula (I).

In one embodiment, the present invention is a chemical compound of structural formula (I), wherein Ar is an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group; k and n are each independently zero or an integer between 1 and 6, provided that k+n≤14; L is selected from —X—, —N(R²)—, —C(X)—, —C(X)X—, —XC(X)—, —C(X)NR²—, —NR²C(X)—, —N(R²)—S(O)$_m$—, —S(O)$_m$—N(R²)—; each X is independently an O or an S; m is 1 or 2; and R, R¹, $R^2$, $R^3$ and $R^4$ for each occurrence is each independently selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkynyl group, C1-C12 alkoxy, or C1-C12 haloalkyl. The values and preferred values of the remainder of the variables are as defined above with respect to formula (I).

In one embodiment, the present invention is a chemical compound of structural formula (I), wherein R, $R^1$, $R^2$, $R^3$ and $R^4$ for each occurrence is independently selected from a hydrogen, a C1-C12 alkyl, a C3-C12 cycloalkyl, a C2-C12 alkenyl, a C3-C12 cycloalkenyl, a C3-C12 cycloalkynyl, a C2-C12 alkynyl, a (C6-C18)aryl(C6-C12)alkyl, or a (C6-C18)heteroaryl(C6-C12)alkyl. Preferably, L is selected from —X—, —N($R^2$)—, —C(X)—, —C(X)X—, —XC(X)—, —C(X)N$R^2$—, —N$R^2$C(X)—. More preferably, $R^1$, $R^2$, $R^3$ and $R^4$ each is hydrogen. In some examples, k and n are each independently 0, 1, 2 or 3. Preferably, X is O. In certain embodiments, Ar is a C6-C18 aryl. Preferably, R for each occurrence is independently selected from a hydrogen, a C1-C12 alkyl, a C3-C12 cycloalkyl, a C2-C12 alkenyl, a (C6-C18)aryl(C6-C12)alkyl, or a (C6-C18)heteroaryl(C6-C12)alkyl; and L is selected from —C(X)—, —C(O)O—, or —OC(O)—. Preferably, k and n is each independently selected from 0, 1 and 2.

In one embodiment, the present invention is a compound represented by the following structural formula:

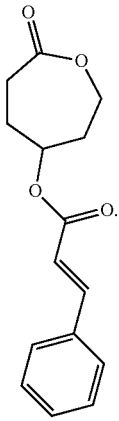

(II)

In another embodiment, the present invention is a compound represented by the following structural formula:

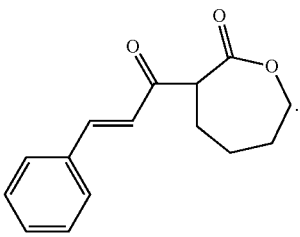

(IX)

In various example embodiments, the polymer of the present invention includes a (co)polymer, in some embodiments derivatives, of polycaprolactone (PCL). A PCL is a polyester of ϵ-caprolactone.

In example embodiments of copolymers of the present invention, PCL can be substituted with a polymer synthesized from a chemical compound represented by a structural formula selected from the group consisting of:

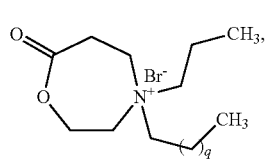

(A)

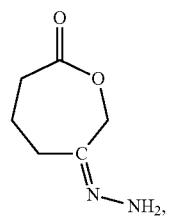

(B)

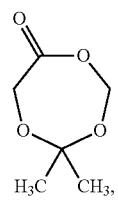

(C)

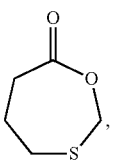

(D)

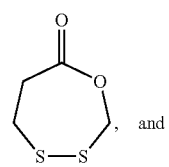

(E)

and

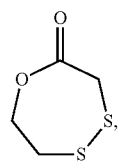

(F)

wherein q is an integer from 1 to 10. In a specific example, q is 4. In another specific example, q is 10.

Alternatively, in example embodiments, PCL can be replaced by a polymer or a random or block copolymer of ϵ-caprolactone and any one or more monomers represented by the structural formulas (A) through (F) reproduced above.

In yet another example embodiment, a (co)polymer suitable for using in the methods of the present invention is a (co)polymer comprising at least one repeat unit represented by the structural formula selected from the group consisting of:

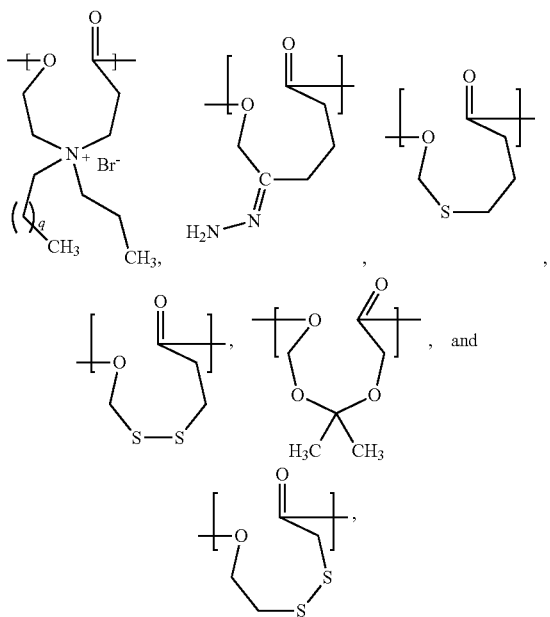

where q is an integers from 1 to 10. In a specific example, q is 4. In another specific example, q is 10.

In another embodiment, the present invention is a polymer comprising at least one repeat unit represented by the following structural formula:

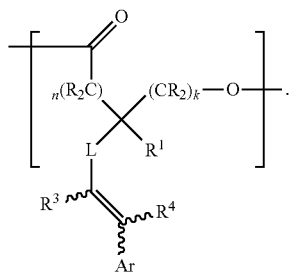
(III)

The values and preferred values of the variables in formula (III) are as defined above with respect to formula (I).

In one embodiment, the present invention is a polymer comprising at least one repeat unit represented by structural formula (III), further comprising at least one repeat unit of the following structural formula:

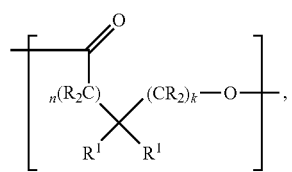
(IV)

wherein $R^1$ for each occurrence independently is as defined with respect to structural formula (III). The values and preferred values of the remainder of the variables are as defined above with respect to formula (I).

Preferably, the polymer of the present invention comprises from 1 to 99% by weight of the repeat units of structural formula (III), preferably, 20-80% by weight, more preferably, 20-50% by weight.

In another embodiment, the polymer of the present invention further comprises at least one initiator. Any initiator commonly used for anionic polymerization can be used. Preferably, the initiator is 2,2'-(ethane-1,2-diylbis(oxy))diethanol. An initiator can include alcoholates and silanolates (($CH_3)_3SiO^-K^+$, $(CH_3)_3SiO^-Na^+$), polyalkoxides (Al(O-i-C3H—)$_3$, Ti(O-n-C$_4$H$_9$)$_4$), oxodialkoxides (Zn[OAl(O-n-C$_4$H$_9$)$_2$]$_2$), monoalkoxides (($C_2H_5)_2AlOCH_3$ (i-C$_4$H$_9$)$_2$AlOCH$_3$, (n-C$_4$H$_9$)$_3$SnOCH$_3$, tetraphenylporphyrin AlOCH$_3$).

In a preferred embodiment, the repeat unit of structural formula (III) is represented by the following structural formula:

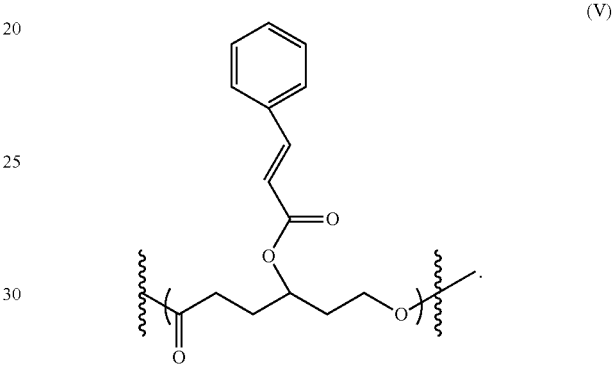
(V)

In another embodiment, the repeat unit of formula (III) is represented by the following structural formula:

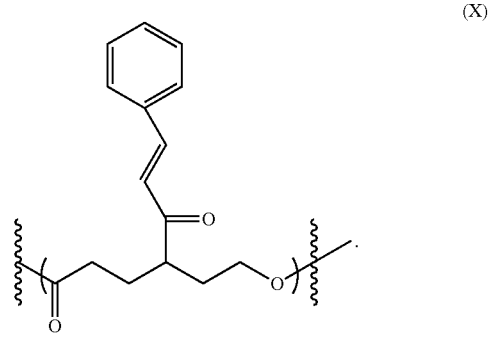
(X)

In another embodiment, the repeat unit of structural formula (IV) is represented by the following structural formula:

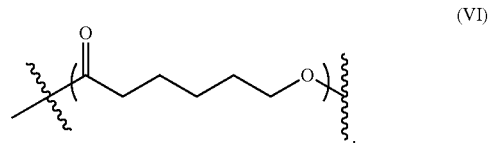
(VI)

Preferably, a polymer of the present invention comprises at least one repeat unit selected from the repeat unit of structural formula (V) or structural formula (X), and further at least one repeat unit of structural formula (VI).

In one embodiment, the present invention is a method of cross-linking a polymer. The method comprises irradiating a starting polymer comprising at least one repeat unit of structural formula (III) with actinic radiation

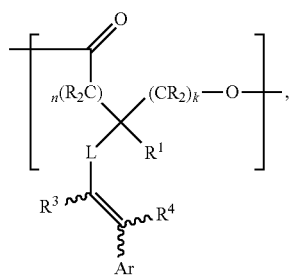

(III)

thereby producing a polymer having at least two cross-linked repeat units represented by structural formulas (VIII) or (VIIIA):

thereby producing a polymer having at least two cross-linked repeat units represented by structural formulas (VIII) or (VIIIa)

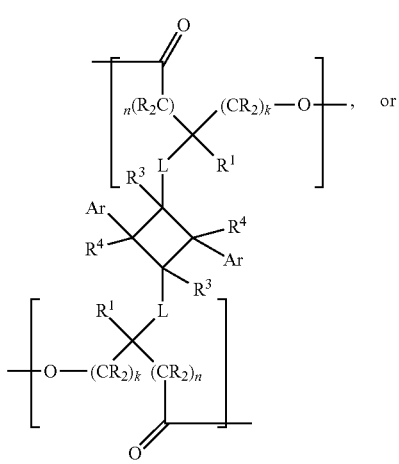

(VIII)

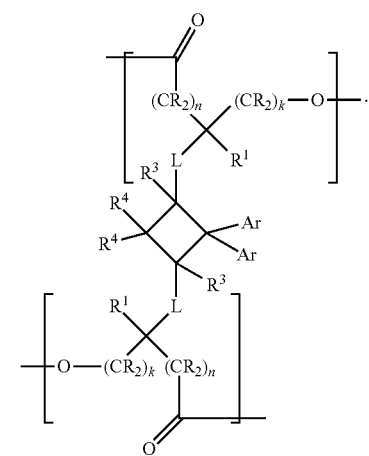

(VIIIA)

Values and preferred values of the variables in structural formulas (VIII) or (VIIIA) are as defined above with respect to structural formulas (I) and (III).

In one embodiment, the starting polymer further comprises at least one repeat unit of the following structural formula:

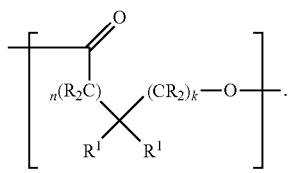

(IV)

Values and preferred values of the variables in structural formula (IV) are as defined above.

In example embodiments, the present invention is a polymer comprising at least one repeat unit represented by the following structural formula:

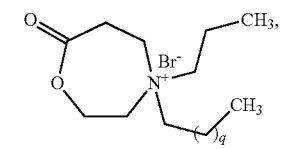

(III)

and at least one repeat unit represented by the structural formula selected from the groups consisting of:

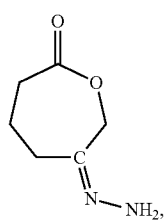

(A)

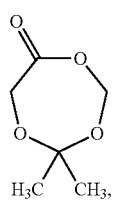

(B)

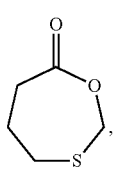

(C)

(D)

-continued

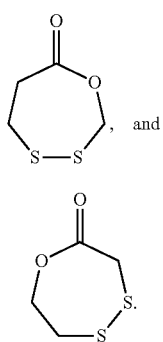

(E)

, and (F)

wherein q is an integer from 1 to 10. Values and preferred values of the remainder of the variables are as defined above with respect to structural formula (III).

Preferably, the starting polymer comprises 1 to 99% by weight of the repeat units of structural formula (III). More preferably, the starting polymer comprises from 20 to 80% by weight, even more preferably, from 20 to 50% by weight of the repeat units of structural formula (III).

In one embodiment, the starting polymer further comprises at least one initiator. Any initiator commonly used for anionic polymerization can be used. For example, the initiator can be 2,2'-(ethane-1,2-diylbis(oxy))diethanol An initiator can include alcoholates and silanolates (($CH_3)_3SiO^-K^+$, $(CH_3)_3SiO^-Na^+$), polyalkoxides ($Al(O-i-C_3H-)_3$, $Ti(O-n-C_4H_9)_4$), oxodialkoxides ($Zn[OAl(O-n-C_4H_9)_2]_2$), monoalkoxides (($C_2H_5)_2AlOCH_3$ $(i-C_4H_9)_2$ $AlOCH_3$, $(n-C_4H_9)_3$ $SnOCH_3$, tetraphenylporphyrin $AlOCH_3$). In one embodiment, the present invention is a method of synthesis of a polymer having at least one subunit represented by the following structural formula

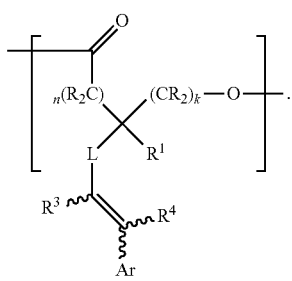

(III)

The method of synthesis comprises reacting a compound of structural formula (I)

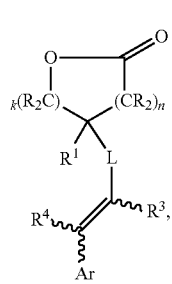

(I)

with a compound of structural formula (VII)

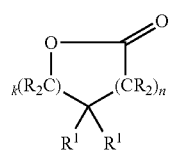

(VII)

thereby producing the polymer having at least one subunit of structural formula (III). Values and preferred values of the variables in structural formulas (I) and (III) are as defined above. Values and preferred values of the variables in structural formula (VII) are as defined above with respect to structural formulas (I) and (III).

In one embodiment, the method of synthesis further comprising the step of producing the compound of structural formula (I) by reacting a compound of structural formula (Ia)

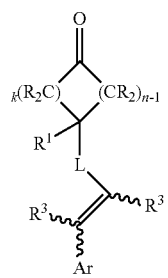

(Ia)

with m-chloroperoxybenzoic acid (m-CPBA), thereby producing the compound of structural formula (I). Values and preferred values of the variables in structural formula (Ia) are as defined above with respect to structural formula (I).

In another embodiment, the method of synthesis further comprising the step of producing the compound of structural formula (I) by reacting a compound of structural formula (VII)

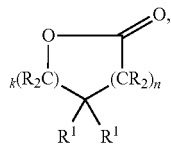

(VII)

with a compound of structural formula (XI)

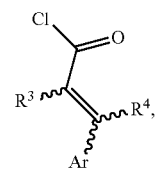

(XI)

thereby producing the compound of structural formula (I). Values and preferred values of the variables in structural formula (XI) are as defined above with respect to structural formula (I). This embodiment is particularly preferred for the synthesis of the compound of formula (IX) and will be described in greater detail in Example 2, below.

Preferably, during the synthesis, from 1 to 99% by weight of the compound Of structural formula (III) is reacted with from 1 to 99% by weight of the compound of structural formula (VII). More preferably, from 20 to 80% by weight of the compound of structural formula (III) is reacted with from 20 to 80% by weight of the compound of structural formula (VII). Even more preferably, from 20 to 50% by weight of the compound of structural formula (III) is reacted with from 50 to 80% by weight of the compound of structural formula (VII).

EXEMPLIFICATION

Example 1

Functionalization of Caprolactone with a Cinnamoyl Moiety (CCL) and Synthesis of the Corresponding Copolymers Materials.

Cinnamoyl chloride (Aldrich, 98%), 1,4-cyclohexanediol (Alfa Aesar, 98+%), Pyridinium chlorochromate (Alfa Aesar, 98%), Triethylamine (Alfa Aesar, 99%), 3-chloroperoxybenzoic acid (Alfa Aesar, 70-75%), ethyl acetate (Aldrich., ~99.5%), triethylene glycol (Aldrich, 99.8%), Hydrochloric acid (Mallinckrodt chemicals, 36.5-38%) sodium chloride (Aldrich, ~99.5%), methylene chloride (Aldrich, ~99.5%), magnesium sulfate (Fluka analytical, 98%), Caprolactone (Alfa Aesar, 99%), Toluene (Aldrich., 99.9%), Tin(II) 2-ethylhexanoate (Sn(Oct)2. Aldrich, 95%), acetic acid (Aldrich, 99.7%), hexane (Aldrich, ~99.8%), tetrahydrofuran, (THF, Aldrich., 99.9%). THF and toluene were distilled over sodium metal and benzophenone under nitrogen atmosphere. Methylene chloride was distilled before the reaction. All other chemicals were used as received.

1. Synthesis of 3-Phenyl-acrylic acid 4-hydroxy-cyclohexyl ester 1,4-cyclohexanediol (20.0 g, 172.4 mmol) was dissolved in dichloromethane (200 mL). Cinnamoyl chloride (7.2 g, 43.1 mmol) dissolved in 50 ml dichloromethane was then slowly added. After 2 h of mixing, triethyl amine (5.3 g, 52 mmol) was added slowly. After 48 h of mixing, the solution was washed three times with dilute HCl (1 M) and two more times with $H_2O$ before it was dried over $MgSO_4$ and filtered. The product was then dissolved in methanol which resulted in precipitation of the byproduct. After filteration and evaporating the solvents from the filtrate, the product was a obtained as yellow-orange viscous liquid, which was used without further purification. Yield: 25-40%.

2. Synthesis of 3-Phenyl-acrylic acid 4-oxo-cyclohexyl ester

Pyridinium chlorochromate (PCC) (19.7 g, 91.5 mmol) was added to a solution of product from step 1 (15.0 g, 61 mmol) in dichloromethane (150 mL). The mixture was stirred for 12 h. The reaction mixture was then added to silica gel (30.0 g) and the solvent was evaporated. The product was purified using column chromatography (by silica gel using hexane/EtOAc gradient as eluent). The product was a white crystalline powder. Yield: 60%.

3. Synthesis of 3-Phenyl-acrylic acid 7-oxo-oxepan-4-yl ester

Product from step 2 (10.0 g, 38.5 mmol) was dissolved in 50 mL of dichloromethane and added dropwise into a solution of 3-chloroperoxybenzoic acid (99.3 g, 42.4 mmol) in dichloromethane (50 mL). The mixture was stirred for 24 h and then filtered. The solution obtained was washed twice with $NaHCO_3$ (2 M) and once with brine. The extracted product was then purified by column chromatography (by silica gel using hexane/EtOAc gradient as eluent). The monomer was obtained as a white crystalline powder. Yield: 70%.

4. Ring Opening Polymerization (ROP) of the Monomers Using $Sn(Oct_2)$

The flask was first filled with nitrogen gas, triethylene glycol (6.3 mg, 0.042 mmol) and ε-caprolactone (5 g, 43.86 mmol) in toluene was added via a syringe into a 100 mL 3-neck round-bottom flask equipped with a stir bar. After a toluene solution of $Sn(Oct_2)$ (1 mol % of carbonyl group, 177.63 mg, 0.44 mmoles) was added, the flask was evacuated for more than 2 hours. Toluene (10 mL per g of monomer) was then added and the reaction flask was immersed in an oil bath at 120° C. for 24 hours (48 hours for CCL) to allow the polymerization to occur. The reaction was quenched by the addition of 0.3 M acetic acid aqueous solution. The flask was then evacuated until a viscous solution was obtained. The reaction mixture was dissolved in tetrahydrofuran and the polymer was precipitated using cold methanol. After filtration and drying in a vacuum at room temperature for 48 hours, the polymer was characterized by NMR and DSC.

Results and Discussion

The synthesis of the new lactone monomer modified with cinnamoyl moiety was performed in three steps. The cinnamoyl moiety was attached to cyclohexandiol by condensation reaction followed by oxidation to get ketone which on further Baeyer Villiger oxidation gave the cinnamoyl modified ε-caprolactone. $^1H$ NMR spectrum showed a peak at 5.3 ppm for —CHrCH—CHr of caprolactone ring indicating successful synthesis of cinnamoyl-caprolactone (CCL). The —COO—CH2-resonated as a multiplet at 4.3 and 4 4.6 ppm. Homopolymer of CCL and copolymers of CCL and ε-caprolactone with different architectures were prepared by anionic ring polymerization (ROP). The synthesis scheme of the polymerization is in FIG. 1. The conversions reported are the extracted weight fraction of the polymer from the polymer work-up. $^1$H-NMR spectrum (not shown) indicated a new resonance at 4.2 ppm for COOCH2CH2- of the carpolactone repeating unit. The —$CH_2OH$ of PCL endgroup was observed at 3.8 ppm. Using end-group analysis, the number average molecular weight, Mn of PCL was calculated to be 45,000. H-NMR spectrum of the random copolymer of CL and CCL showed a new resonance at 4.3 ppm for —COOCH2CH2- of the modified carpolactone (CCL) repeating unit. The —CH2OH of copolymer end-group was observed at 3.8 ppm, using end-group analysis, the M" of PCL was calculated to be 59,000. The mole fraction of monomer in the feed was 1:1 (i.e. CL:CCL=1:1) but the final polymer contains monomers in ratio of CL:CCL=0.65:0.35. CCL has the cinnamoyl group at the γ position and its effect on the ring carbonyl was to be low. Hence, the reactivity of the CL and CCL was expected to be same.

For the CCL homopolymer, the —COOCH$_2$CH$_2$— resonance of the cinnamate-modified carpolactone (CCL) repeating unit was seen at 4.1 ppm. The resonance of —CH$_2$CHCH$_2$— and —CH$_2$CHCH$_2$— of PMCL was observed at 5.1 ppm and 2.3 ppm respectively. The low yield of the polymer can be attributed to a low concentration of the co-catalyst. It is speculated that the co-catalyst may be coordinating with the carbonyl of the cinnamoyl group resulting in low overall concentration of the co-catalyst available for the polymerization. This effect is also seen with the decrease in yield of the polymer with increasing concentration of CCL.

Figure 2:
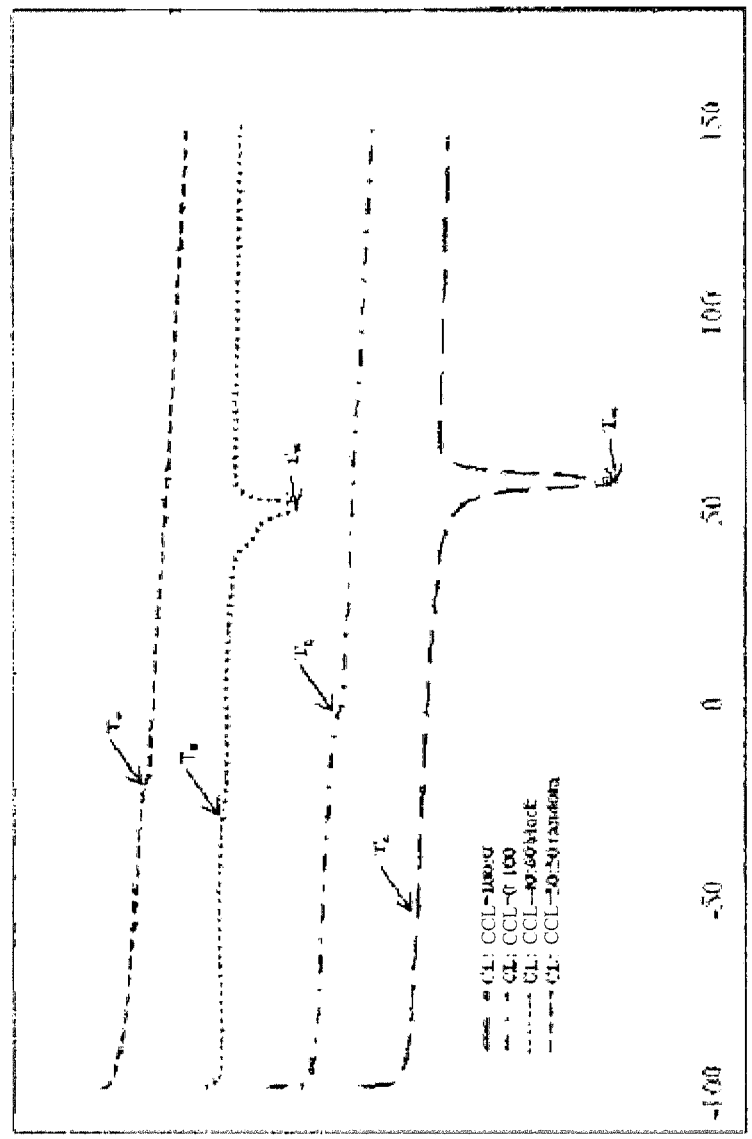
FIG. 2 is differential scanning calorimetry traces of the un-crosslinked polymers of the present invention.

The DSC traces of the un-crosslinked polymers are shown in FIG. 2. The second heating cycle is taken so as to neglect any thermal history due to processing seen in the first heating cycle. PCL gave a glass transition temperature (Tg) at −62° C. and a melting transition (Tm) at 57° C. With the incorporation of CCL, the Tm completely disappeared. This can be seen in both the homopolymer of CCL and random copolymer of CCL and CL will the random copolymer the pendant cinnamoyl group affects the crystalline packing of the chains resulting in amorphous polymers with Tg at −25° C. The homopolymer of CCL gave no Tm but has a Tg at 40° C. With the incorporation of the CCL, the Tg increased due to the increase in the aromatic character of the polymers which decreased the mobility of the chains and hence, increased the Tg. The block copolymer gave the Tm at 51° C. The decrease in melting point is expected due to a decrease in the mobility of chains at the ends due to CCL and smaller crystalline domains in the copolymer.

The synthesis of a new lactone monomer modified with cinnamoyl moiety, a potentially-curable unit was successfully accomplished. Homopolymer of CCL and copolymers of CCL and ε-caprolactone prepared with different architectures were by anionic ring opening polymerization (ROP).

$^1$H NMR spectrum showed a new resonance at 4.2 ppm for —COOCH$_2$CH$_2$— of the carpolactone repeating unit. The —CH$_2$OH of PCL end-group was observed at 3.8 ppm. Using end-group analysis, the number average molecular weight, $M_n$ of PCL was calculated to be 45,000.

$^1$H NMR spectrum of the random copolymer of CL and CCL showed a new resonance at 4.3 ppm for —COOCH$_2$CH$_2$— of the modified carpolactone (CCL) repeating unit. The —CH$_2$OH of copolymer end-group was observed at 3.8 ppm. Again, using end-group analysis, the $M_n$ of PCL was calculated to be 59,000. The mole fraction of monomer in the feed was 1:1 i.e. CL:CCL=1:1 but the final polymer contains monomers in ratio of CL:CCL=0.65:0.35. CCL has the cinnamoyl group at the γ position and its effect on the ring carbonyl was assumed to be low. Hence, the reactivity of the CL and CCL was expected to be same.

Figure 3:
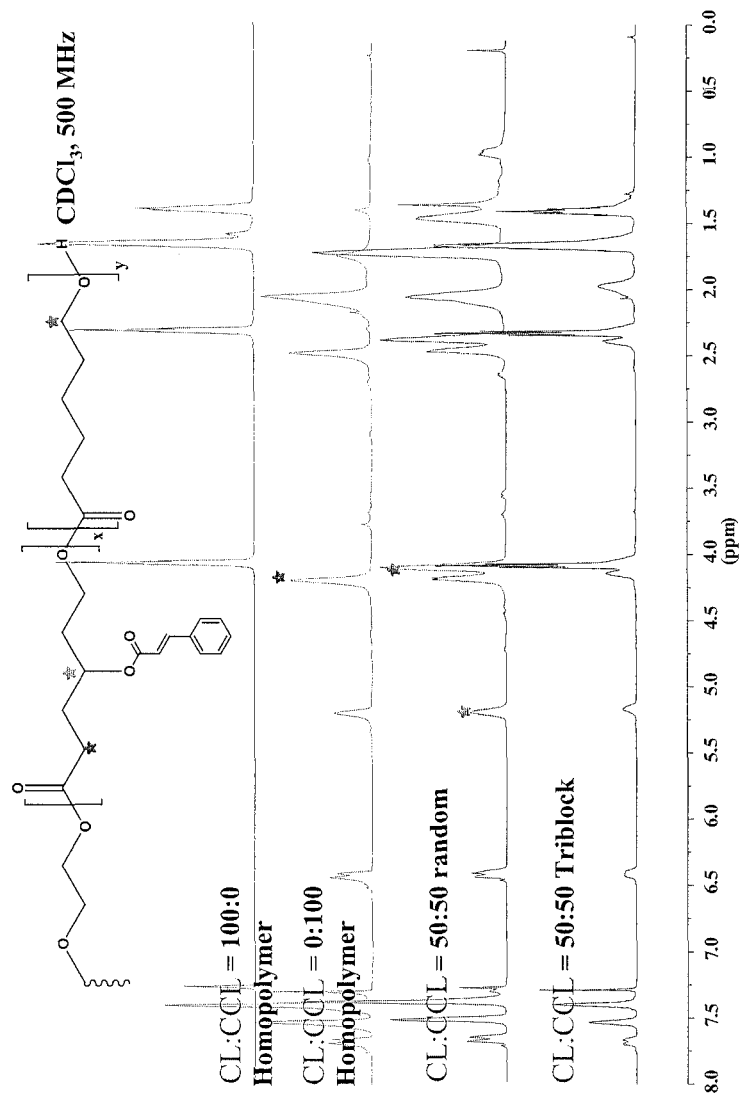
FIG. 3 depicts $^1$H-NMR spectra of selected polymers of the present invention.

For the CCL homopolymer, the —COOCH$_2$CH$_2$— resonance of the cinnamate-modified carpolactone (CCL) repeating unit was seen at 4.1 ppm. The resonance of —CH$_2$CHCH$_2$— and —CH$_2$CHCH$_2$— of PCCL was observed at 5.1 ppm and 2.3 ppm respectively shown in FIG. 3.

The curing of the resulting copolymer and the analysis of their mechanical properties are currently in progress.

Example 2

Synthesis of the Compound of Structural Formula (IX)

The compound of formula (IX)

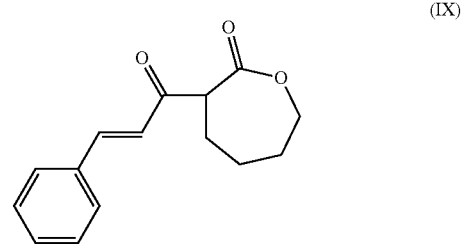 [SMILES: O=C(/C=C/c1ccccc1)C1CCCCOC1=O]

was synthesized according to the following synthetic scheme:

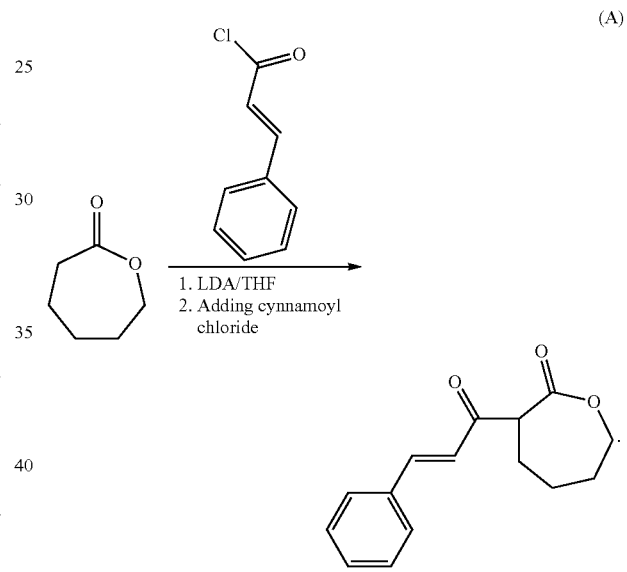

ε-caprolactone was modified to obtain an aromatic or carboxylic group on the core-forming block as shown in Scheme (A). Anionic activation of ε-caprolactone monomer was performed using a freshly prepared non-nucleophilic strong base diisopropylamine (LDA) to extract a methylene proton from the α-position (—CH2-C═O). The generated lithium carbanion was then quenched with cinnamoyl chloride to obtain an α-cinnamoyl-ε-caprolactone derivative. After column chromatography the modified ε-caprolactone was isolated as a white solid. The yield of the reaction was about 30%. The structure was confirmed by a combined analysis of $^1$H NMR, $^{13}$C NMR, 2D-NMR Example 3

Post-Modification of Polymer

Bu—Li (24 mL) in hexane was slowly added to dry diisopropylamine (8.4 mL) in 60 mL of dry THF in a three-neck round-bottomed flask at −30° C. under vigorous stirring with continuous argon supply. The solution was cooled to −78° C. Poly(ε-Caprolactone) (3.42 g) was dissolved in 8 mL of dry THF and added to the above-mentioned mixture slowly, followed by the addition of Cinnamoyl chloride (5.1 g). The temperature was allowed to rise to 0° C., and the reaction was quenched with 5 mL of saturated ammonium chloride solution. The reaction mixture was diluted with water and extracted with dichloromethane. The combined extracts were dried over $Na_2SO_4$ and evaporated. The polymer is than dissolved in THF and precipitated with cold methanol.

The chemical structure can be analyzed by $^1$H NMR, $^{13}$C NMR, IR, and mass spectroscopy.

Example 4

Selecting Molecular Weight of Starting Polycaprolactone Macromers Affects Transition Temperature of the Resulting Tri-Block Copolymer Measurement of Linear Viscoelastic Thermomechanical Properties of the Polymers Measurement of linear viscoelastic thermomechanical properties of the polymers were conducted using a dynamic mechanical analyzer (DMA) (TA Instruments, Model Q800). The DMA was employed in tensile mode with a preload force of 1 mN, an oscillation amplitude of 5 μm (less than 0.18%), static stress/dynamic stress amplitude ratio (force tracking) of 110%, and an oscillation frequency of 1 Hz. The one-way shape memory experiment was performed in the stress-controlled mode, according to the methods known in the art. (See, Rousseau et al. *J. Am. Chem. Soc.*, 2003, 125, 15300-15301.) Samples (in tension with a preload force of 0.001 N) were equilibrated at 60° C. The samples were then elongated to a force of 0.024 N at a rate of 0.005 N min$^{-1}$, cooled at a rate of 3° C. min$^{-1}$ to 0° C. in order to fix the elongated shape, and unloaded to 0.001N using the same rate as before, 0.005 N min$^{-1}$. The samples were then recovered by heating at the rate of 3° C. min$^{-1}$ to 60° C. The shape fixity ratio, $R_f$ and the shape recovery ratio, $R_r$ are used to quantify the shape memory behavior. $R_f$ is related to the fixation of the temporary shape and is a measure for the fixability of a mechanical deformation $\epsilon_i$, $R_r$ describes to what extent the original shape can be recovered. The percentage of shape fixing, $R_f$, and shape recovery, $R_r$ were calculated using the following equations.

$$R_f(\%) = \left(\frac{\varepsilon_u(N)}{\varepsilon_i(N)}\right) \times 100,$$

$$R_r(\%) = \left(\frac{\varepsilon_u(N) - \varepsilon_f(N)}{\varepsilon_u(N) - \varepsilon_f(N-1)}\right) \times 100$$

In the above equations, $\epsilon_u$ is the strain obtained after releasing the applied load, $\epsilon_i$ is the initial strain before the load was released, and $\epsilon_f$ is the final strain after heating with no applied load, i.e. after maximum recovery of the deformation and N is the number of cycles.

Synthesis

Tri-block copolymers of general formula X-Y-X, where X is a polycaprolactone macromonomer (PCL) and Y is cinnamate-modified ε-caprolactone (CCL) were synthesized as described above. In the experiments described below, the subscript next to "PCL" denotes the molecular weight, in grams per mol, of the starting PCL diol macromonomer (i.e. a macromonomer initiator). The ratio of two numbers (e.g., 50:50) denotes the ratio (by weight) of the two combined PCL blocks (X) to the CCL block (Y). Thus, for example, "50:50 (triblock PCL$_{1250}$)" denotes a triblock copolymer X-Y-X, in which the first and the third Xs are polycaprolactone diol macromonomers, the Y is a polymerized CCL, the weight ratio of (X+X)/Y is 50:50, and PCL diol of the molecular weight of 1250 g/mol and 2000 g/mol was used as a macromonomer initiator.

The molecular weight distribution and the polydispersity index ($M_w/M_n$ or PDI) of the copolymers were determined using THF-GPC against linear poly(styrene) (Table 1). The GPC chromatograms of the polymers showed a broad distribution as seen from the PDIs listed in Table 1 and the $M_n$ obtained was in good agreement with the targeted molecular weight of each type of polymer. Uniform thin films were obtained for curing and testing of the mechanical and shape memory effect post-curing.

TABLE 1

Yield, composition and molecular weights of copolymers of CL and CCL

| Copolymer (CL:CCL)$^a$ | Reaction time (hr) | Yield$^b$ (wt %) | $M_n{}^c$ (g mol$^{-1}$) | $M_w/M_n{}^c$ | CCL in Polymer (%)$^d$ |
|---|---|---|---|---|---|
| 100:0 | 24 | 95 | 28,000 | 2.40 | 0 |
| 50:50 (triblock) | 36 | 60 | 8,800 | 2.10 | 22 |
| 50:50 (random) | 24 | 90 | 7,100 | 1.58 | 45 |
| 0:100 | 24 | 50 | 6,670 | 1.61 | 100 |
| 50:50 (triblock PCL$_{1250}$) | 24 | 70 | 11,700 | 1.26 | 35 |
| 50:50 (triblock PCL$_{2000}$) | 24 | 65 | 10,100 | 1.1 | 25 |

$^a$The ratio of monomers in the feed, corresponding to the theoretical ratio of monomers in the polymer.
$^b$Weight of polymer obtained after precipitation in cold methanol.
$^c$Determined by GPC in THF relative to linear polystyrene standards.
$^d$Determined via integration of $^1$H NMR spectra in CDCL$_3$.

Using anionic polymerization, polymers with controlled or desired molecular weight were expected. But due to side reactions such as transesterification reaction of the attached cinnamoyl group, low conversions were obtained and the polydispersity of the polymers was high. Hence, the control of the polymerization was compromised. While the conversion of CCL is significantly slower compared to the more reactive CL under the applied conditions, this alone cannot explain the results. It is postulated that the low conversion and high polydispersity are due to side reactions such as inter- and intra-transesterification of both the polyester backbone as well as the pendant cinnamate group.

To fine-tune and control the transition temperature (the temperature at which the polymer switches from a permanent shape to a temporary shape), PCL diols with $M_w$ 1,250 and 2,000 g mol$^{-1}$ were used as macroinitiators for the copolymerization with CCL. The results of the polymerization are included in Table 1. Triblock copolymers with higher molecular weight and better polydispersity were obtained. The incorporation of CCL into the copolymer was similar to the previous triblock copolymer (i.e. the percent composition was similar).

Shape Memory Properties

Actuation of the shape transition is induced by heat. All the polymers synthesized showed very low glass transition temperatures which are not suitable for on-demand shape memory transition for biomedical applications. Only the triblock copolymers showed a $T_m$. Utilizing the melting temperature of the triblock copolymer as the transition or switching temperature, $T_{trans}$, the one-way shape memory effect was characterized. For shape programming and recovery the thermomechanical cyclic experiments were performed in a stress-controlled mode according to the procedures known in the art. (See, for example, Nagata et al. *J. Polym. Sci., Part A: Polym. Chem.* 2005, 43, 2426-2439; Nagata et al. *Colloid Polym. Sci.* 2006, 284, 380-386; Nagata et al. *J. Polym. Sci., Part A: Polym. Chem.* 2009, 47, 2422-2433; Rousseau et al. *J. Am. Chem. Soc.*, 2003, 125, 15300-15301; and Lendlein et al. *Science*, 2002, 296, 1673-1676, the relevant portions of which are incorporated herein by reference.)

Figure 4:
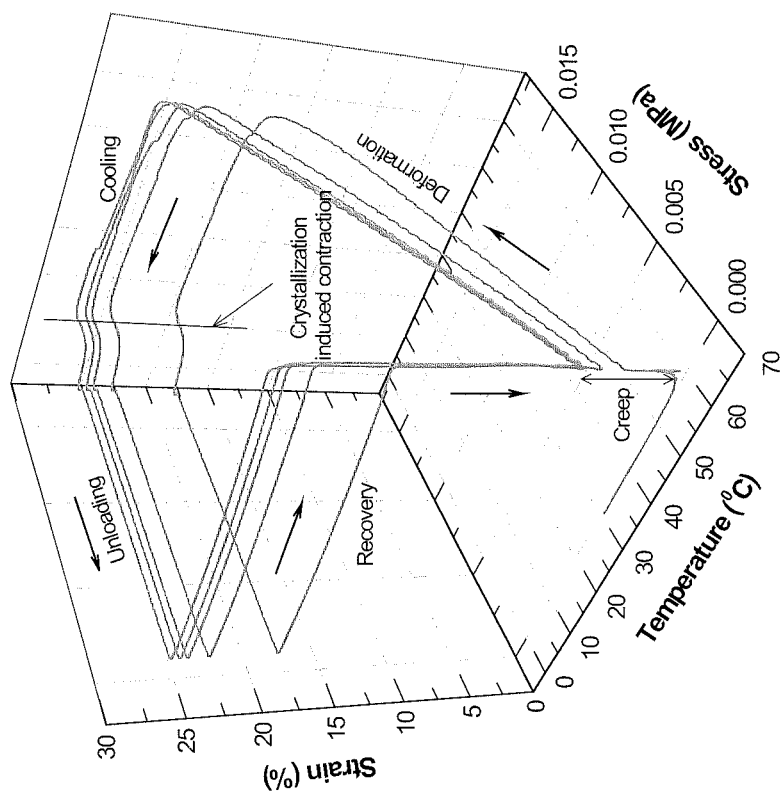
FIG. 4 depicts a 3D diagram of $T_m$-based one-way shape memory cycle for a poly(CL:CCL) 50:50 triblock copolymer described in Example 4.

The three-dimensional (3-D) test record for our poly(CL:CCL)=50:50 triblock copolymer-based networks is given in FIG. 4. This shape memory cycle consists of four consecutive segments. In the first step, the sample is deformed at a temperature above $T_m$ to 60° C., resulting in an increase of strain (deformation) from 19% in the first cycle to a maximum of 25% in the fifth cycle.

In the second step, the sample is cooled below $T_m$ to 0° C. under constant tensile stress ($\sigma$) to freeze the extended strain, ($\epsilon$) (cooling). The change in strain in this region is influenced by the temperature dependence of the coefficient of thermal expansion of the stretched polymer and volume effects that is based on the thermal transition at $T_{trans}$, e.g. a crystallization process. While cooling the sample, strain initially increases due to the creep response of the material under constant stress. As the temperature decreased below 20° C., the sample began to contract due to crystallization-induced contraction. The triblock has a crystallization temperature of 22° C. The strain then reached a plateau as the sample vitrifies below crystallization temperature. In the third step, the applied stress is reduced to the preload value (0.001 N) at 0° C., and the strain remains constant (unloading and shape fixing).

The mechanical movement in the course of the shape-memory effect is so recorded as a function of the temperature. As indicated in FIG. 4, the DMA cycles can differ from each other. With an increasing number of cycles the curves become more similar. The low recovery of the polymer in the $1^{st}$ cycle is due to irreversible creep in the polymer after the $1^{st}$ cycle. This creep increased slightly until the $2^{nd}$ cycle and remained approximately constant with each subsequent cycle. The process of deformation and recovery of the permanent shape becomes highly reproducible. The changes in the first cycles are attributed to the history of the sample piece. With respect to this, processing and storage play an important role. During the first cycles a reorganization of the polymer on the molecular scale takes place. This is a reaction on the deformation in a certain direction. After the $2^{nd}$ cycle, the triblock showed excellent shape recovery $R_r$ of approximately 99% of the initial strain. As seen from Table 2, the shape fixity $R_f$ was excellent with approximately 99% of the initial strain retained after unloading of the stress.

TABLE 2

Strain, Shape Fixation ($R_f$), and Shape Recovery ($R_r$) of Crosslinked Triblock Copolymer.

| Cycle No. | Strain (%) | $R_f$ (%) | $R_r(1^{st})$ (%) | $R_r(2^{nd})$ (%) |
|---|---|---|---|---|
| 1 | 18.86 | 98.73 | 59.89 | 65.61 |
| 2 | 23.52 | 98.98 | 80.37 | 92.72 |
| 3 | 24.91 | 99.04 | 83.75 | 98.93 |
| 4 | 25.41 | 99.06 | 84.24 | 99.42 |
| 5 | 25.99 | 99.04 | 85.11 | 99.61 |

$R_r(1^{st})$: Instantaneous recovery at 60° C.
$R_r(2^{nd})$: Recovery after 30 minutes of isothermal heating at 60° C.

In the fourth step, the sample is now heated up to $T_{high}$=60° C. in a controlled way and the extended strain starts to recover when the temperature exceeds $T_m$ of the sample (recovery). The temperature is held at 60° C. for additional 30 min to recover any residual strain (recovery). Also seen in Table 2, two recovery rates are observed for the sample. The sample have very high initial recovery rate, $R_r(1^{st})$ with approximately 85% of the strain recovered instantaneously. The recovery of the remaining strain is slow requiring 30 minutes of isothermal heating. The driving force for the sample recovery is the stress imposed on the material during shape programming. As the sample recovers, the driving force is decreased leading to a slow recovery. The slow recovery could also be attributed to irreversible deformation of the sample driven by the preload force.

Figure 5:
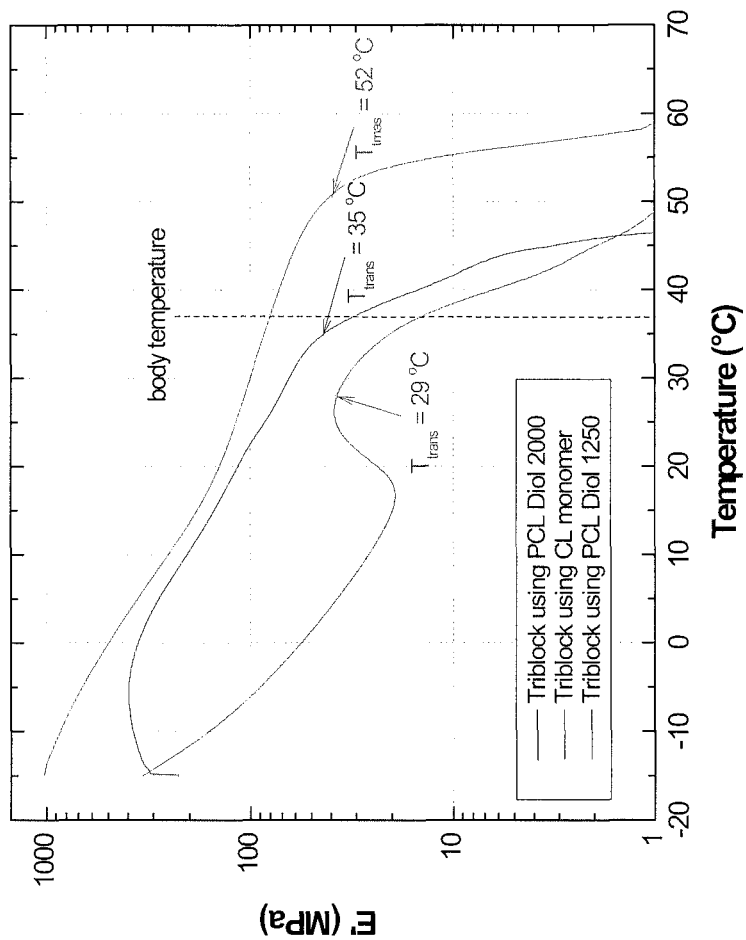
FIG. 5 is a plot of tensile storage modulus (E') as a function of temperature for three tri-block polymer examples of the present invention.

To investigate this behavior, DMA measurements above $T_m$ was performed and shown in FIG. 5 as a plot of storage modulus, E as a function of temperature. At 60° C., the sample has a modulus of 0.8 MPa. Thus, under a preload force of 0.001 N, the deformation of the sample is rather small (approximately 0.16%). Subsequently, the slow recovery is not due to deformation, but instead can be explained by dissipation of some of the stress by chain relaxation at temperatures above $T_m$.

Crosslinking is necessary for shape memory trigger, if the highest transition temperature of the polymer is being used. Shape memory effect based on the $T_m$ of PCL was successfully demonstrated. If instead, the $T_g$ of the P(CL:CCL) triblock copolymer was used for the trigger, then crosslinking would be unnecessary if the material is able to hold its permanent shape. In order to confirm this hypothesis "control" experiments were performed using the uncrosslinked triblock copolymers and the crosslinked random copolymers. The uncrosslinked triblock copolymer was heated above $T_m$, it melted and would not hold its shape. Hence, thermomechanical cycling experiments using the DMA was not possible to be performed with the uncrosslinked triblock copolymers. Similarly, the random copolymer did not hold its shape at 60° C. Thus, for SMP systems in which the transition temperatures are closely based on the $T_m$, both crystallinity and crosslinking is necessary to achieve a shape memory effect.

The dynamic mechanical behavior of the poly(CL:CCL) (50:50) triblock copolymer networks were found to depend strongly on molecular weight of the PCL, as shown in FIG. 5. The temperature at which the onset of decline in the tensile storage modulus occurs was found to coincide with the transition temperature ($T_{trans}$) for the shape memory effect. It was found that $T_{rans}$ increased as the macromomer molecular weight increased. This effect resulted for semicrystalline networks having a strongly sloped tensile storage modulus between the PCL $T_g$ and $T_m$ and its strong dependence on the molecular weight of the PCL. The ability to tune the switching temperatures is an unexpected and beneficial property that lends itself to different applications.

Example 5

Synthesis and Advantageous Properties of Selected Monomers Employed in (Co)Polymers of the Invention (1) Amine-Functionalized $\epsilon$-Caprolactone Monomer Having Antimicrobial Properties Microbial infection remains one of the most serious complications in several areas, particularly in medical devices, drugs, health care and hygienic applications, water purification systems, hospital and dental surgery equipment, textiles, food packaging, and food storage. Antimicrobial agents capable of being incorporated into other materials gain interest from both academic research and industry due to their potential to provide quality and safety benefits to many materials. However, low molecular weight antimicrobial agents suffer from many disadvantages, such as toxicity to the environment and short-term antimicrobial ability. To overcome problems associated with the low molecular weight antimicrobial agents, antimicrobial functional groups can be introduced into polymer molecules. The use of antimicrobial polymers offers promise for enhancing the efficacy of some existing antimicrobial agents and minimizing the environmental problems accompanying conventional antimicrobial agents by reducing the residual toxicity of the agents, increasing their efficiency and selectivity, and prolonging the lifetime of the antimicrobial agents.

Quaternary ammonium compounds (QACs) possess antimicrobial properties. Common characteristics among QACs are that they possess both a positive charge and a hydrophobic segment. Classification and biological activity of QACs depend upon the nature of the organic groups attached to nitrogen, the number of nitrogen atoms present, and the counterion.

Each of the ε-caprolactone derivatives can be generated by the Baeyer-Villiger oxidation of the corresponding cyclohexanone derivative. Monoprotection of 1,4-cyclohexanediol by benzylation or esterification is accomplished in moderate yields by reaction of benzyl bromide or 2,2'-bis(phenyldioxymethyl)propionyl chloride. Each compound is oxidized with pyridinium chlorochromate to yield the respective protected hydroxyl and bis(hydroxyl) functional cyclohexanones. The benzyl ether and benzyl ester protecting groups can be readily removed by catalytic hydrogenolysis using Pd/C.

Scheme 1 illustrates synthesis of Monomer (A).

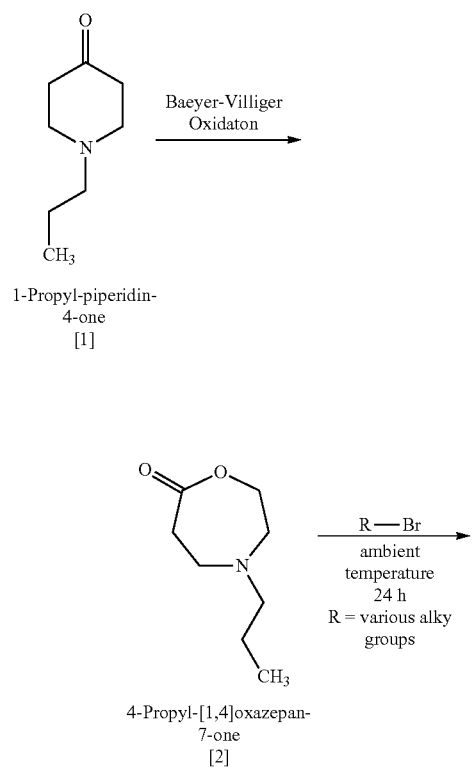

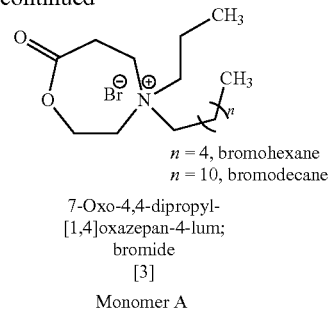

n = 4, bromohexane
n = 10, bromodecane

7-Oxo-4,4-dipropyl-
[1,4]oxazepan-4-Ium;
bromide
[3]

Monomer A

According to one example of Scheme 1,4-Propyl-[1,4]oxazepan-7-one [2] (0.102 mol) was dissolved in 80 mL ethyl acetate in a 100-mL round-bottomed flask. The solution mixture was stirred for 10 min to dissolve [2] completely, and then 1-bromobutane (0.140 mol) was added to the flask containing the [2] solution. The flask was closed with a rubber septum to prevent the absorption of water by the salt being formed. 1-Bromobutane was used in excess to ensure that all [2] reacted, as it is more easily removed from the final product than unreacted [2]. After 5 min, the formation of a white solid product was observed and the reaction was continued for 24 h. The salt formed was filtered from the solution by suction filtration and washed once with ethyl acetate and then three times with diethyl ether. It was dried over $P_2O_5$ at room temperature in a vacuum oven to remove trapped solvents to give product [3] (22.35 g) in 93% yield. This same procedure was applied to the reaction of [2] with 1-bromohexane. [2] (0.05 mol) and 1-bromohexane (0.06 mol) reacted in ethyl acetate (50 mL) to give product [3] (12.49 g) in 90% yield.

Monomers A can be copolymerized with cinnamoyl functionalized caprolactone to give triblock copolymers (XYX, where X is a polymer of monomer A and Y is a polymer of cinnamoyl functionalized caprolactone) with a molecular weight region between $5 \times 10^4$ and $1.2 \times 10^5$ Da optimal for the required action.

The quaternary ammonium polymers synthesized can have counterions of bromide or chloride, with bromide anions being preferable for increased biocides potency. Potential applications for these triblock copolymers include but not limited to in medical devices, drug delivery vehicles, and health care and hygienic applications, water purification systems, hospital and dental surgery equipment, textiles, food packaging, and food storage. The use of long-term catheters can lead to serious implant associated infections.

(2) Copolymers Having Controlled Biodegradation Rates

Introducing various functionalities in the monomer provides a mechanism to control the availability of functional pendant groups along the polymer backbone. These functionalized monomers can be copolymerized with cinnamoyl functionalized caprolactone to give triblock copolymers. These monomers introduce various stimuli sensitive functional groups in the backbone of the copolymers. On applying a stimulus, the backbone of the polymer gets affected. These can be used to control properties such as biodegradation rate, mechanical properties. This would be a highly efficient means of tailoring the properties of polyesters including features such as hydrophilicity, biodegradation rates, bioadhesion, drug attachment, mechanical properties. A rational approach for controlling the biodegradation rate is to change the polarity by cleaving covalent bonds, which is generally irreversible. On the other hand, a reversible change in polarity can be the result of changes of the hydrogen bonding capability (temperature sensitive polymers), by protonation (pH-sensitive polymers), or by changes of the redox potential. Another strategy concerns the use of light as an external stimulus, which can induce both reversible and irreversible changes in the polarity of block copolymers.

pH-Sensitive Acid-Labile Poly(ε-Caprolactone) Derivatives pH-sensitive, acid-labile monomers B and C can be synthesized as described below:

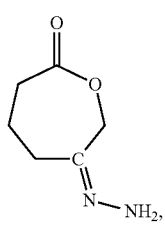

Monomer B

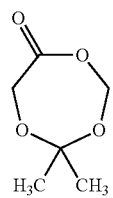

Monomer C

The use of an acid-labile hydrazone linkage in Monomer B facilitates pH responsive degradation. In N,N'-dialkylhydrazone-functionalized caprolactone, the C=N bond can be hydrolyzed, oxidized and reduced, the N—N bond can be reduced to the free amine. When Monomer C is copolymerized with cinnaomoyl functionalized caprolactone, a lower pH at around 4.5 can break the backbone of the copolymer and release non-acidic byproducts. By varying the content of Monomer C in the copolymer, degradation rate can be controlled with no acidic byproducts. Also as the backbone of the copolymer breaks, the mechanical properties can change.

Monomer C was prepared according to Scheme 2:

Scheme 2.

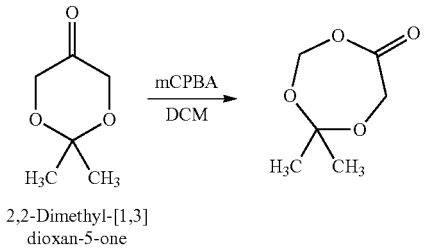

2,2-Dimethyl-[1,3]dioxan-5-one 2,2-Dimethyl-[1,3]dioxan-5-one can be dissolved in dichloromethane (DCM) and added dropwise into a solution of 3-chloroperoxybenzoic acid (m-CPBA) in DCM. The mixture is stirred for 24 h and then filtered. The resulting solution is washed twice with NaHCO₃ (2 M) and once with brine. The extracted product is then purified by column chromatography (by silica gel using hexane/EtOAc gradient as eluent). The Monomer C is obtained as a white crystalline powder.

In addition, when Monomer C is copolymerized with cinnamoyl-caprolactone to give a triblock copolymer, an acid-sensitive drug delivery vehicle could be achieved, designed to target therapeutics to the acidic environments of tumors, inflammatory tissues, and phagosomes. Monomer C is a hydrophobic monomer that contains ketal linkages that can undergo acid-catalyzed hydrolysis into low molecular weight hydrophilic compounds and should therefore release encapsulated therapeutics at an accelerated rate in acidic environments. Importantly, the resulting polyketal/cinnamoyl caprolactone triblock copolymer does not generate acidic degradation products after hydrolysis, as with polyester-based biomaterials. This new delivery system should find numerous applications in the field of drug delivery bioimplants (e.g. stents) because of its ease of synthesis and excellent degradation properties.

Oxidation-Responsive ε-Caprolactone Derivative

Monomer D is an ε-caprolactone derivative responsive to oxidation:

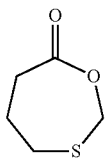

Monomer D

When copolymerized with PCL diols to give a triblock copolymer XYX, where X is PCL and Y is a polymer of Monomer D, upon exposure to oxidative agents, the thioethers in the block copolymer is oxidized to the corresponding sulphoxide and eventually to the sulphone, leading to the hydrophilization of the original hydrophobic block copolymer.

Reduction-Responsive ε-Caprolactone Derivative

Monomers E and F are ε-caprolactone derivative responsive to reduction:

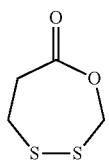

Monomer E

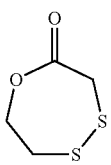

Monomer F

The disulfide bonds in Monomers E and F are reduction sensitive. Intracellular glutathione (GSH), the most abundant intracellular reducing agent present in concentrations up to 10 mM in tissues, will reductively cleave these links which will lead to biodegradation. Applying a reduction stimulus to (co)polymers made from monomers E and F, a crosslinking reaction between (co)polymer chains is triggered, that would change its mechanical properties.

Monomers E and F were synthesized according to the Scheme 3:

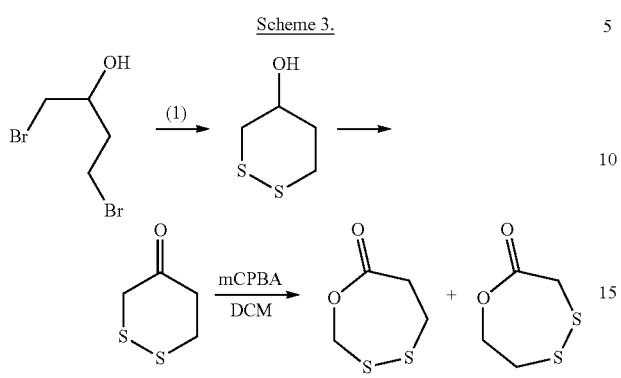

In Scheme 3, reaction (1) was accomplished as described in *Tetrahedron Letters,* 2008, 49, 520-522, the relevant portion of which is incorporated herein by reference. Briefly, didecyldimethylammonium bromide (DDAB) catalyzed the formation of cyclic disulfides from the corresponding n-dibromo compounds in moderate to excellent yields under mild conditions. The process afforded symmetrical as well as unsymmetrical cyclic disulfides. The reaction was fast, and was carried out at room temperature. In a generalized procedure, 1,4-dibromo-2-butanol (in chloroform) was stirred with aqueous sodium sulfide and sulfur in the presence of DDAB as a phase transfer catalyst at room temperature. The yield of the corresponding cyclic disulfide was high (90%) with complete conversion of the starting dihalide.

EQUIVALENTS

While this invention has been particularly shown and described with references to example embodiments thereof, it will be understood by those skilled in the art that various changes in form and details may be made therein without departing from the scope of the invention encompassed by the appended claims.

The invention claimed is:

1. A polymer comprising at least one repeat unit represented by the following structural formula:

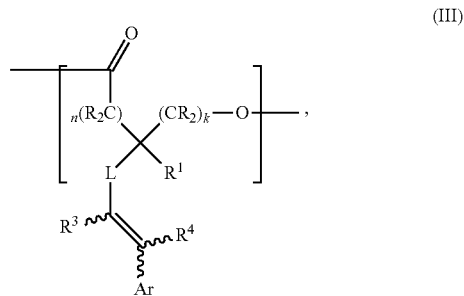

wherein:
Ar is an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group;

k and n are each independently zero or an integer between 1 and 6, provided that k+n≤14;

L is selected from
—X—, —N($R^2$)—, —C(X)X—, —XC(X)—, —C(X)N$R^2$-, —N$R^2$C(X)—, —N($R^2$)-S(O)m-, —S(O)m-N($R^2$)-;

each X is independently an O or an S;

m is 1 or 2; and

R, $R^1$, $R^2$, $R^3$, and $R^4$ for each occurrence is independently selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkyne group, C1-C12 alkoxy, or C1-C12 haloalkyl.

2. The polymer of claim 1, further comprising at least one repeat unit of the following structural formula:

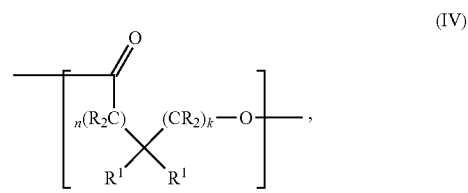

wherein $R^1$ for each occurrence independently is as defined in claim 1.

3. The polymer of claim 2, wherein the polymer comprises from 1 to 99% by weight of the repeat units of structural formula (III).

4. The polymer of claim 3, wherein the polymer comprises from 20 to 50% by weight of the repeat units of structural formula (III).

5. The polymer of claim 1, further comprising at least one initiator.

6. The polymer of claim 4, wherein the initiator is of 2,2'-(ethane-1,2-diylbis(oxy))diethanol.

7. The polymer of claim 2, wherein R, $R^1$, $R^2$, $R^3$ and $R^4$ for each occurrence is independently selected from a hydrogen, a C1-C12 alkyl, a C3-C12 cycloalkyl, a C2-C12 alkenyl, a C3-C12 cycloalkenyl, a C3-C12 cycloalkynyl, a C2-C12 alkynyl, a (C6-C18)aryl(C6-C12)alkyl, or a (C6-C18)heteroaryl(C6-C12)alkyl.

8. The polymer of claim 7, wherein L is selected from —X—, —N($R^2$)—, —C(X)X—, —XC(X)—, —C(X)N$R^2$—, —N$R^2$C(X)—.

9. The polymer of claim 8, wherein $R^1$, $R^2$, $R^3$ and $R^4$ each are hydrogen.

10. The compound of claim 9, wherein k and n are each independently from 0 to 3.

11. The polymer of claim 10, wherein X is O.

12. The polymer of claim 9, wherein Ar, for each occurrence independently, is a C6-C18 aryl.

13. The polymer of claim 12, wherein:
R for each occurrence independently is selected from a hydrogen, a C1-C12 alkyl, a C3-C12 cycloalkyl, a C2-C12 alkenyl, a (C6-C18)aryl(C6-C12)alkyl, or a (C6-C18)heteroaryl(C6-C12)alkyl; and
L for each occurrence independently is selected from —C(O)O—, or —OC(O)—.

14. The compound of claim 13, wherein k and n are each independently from 0 to 2.

15. The polymer of claim 14, wherein the repeat unit of structural formula (III) is represented by the following structural formula:

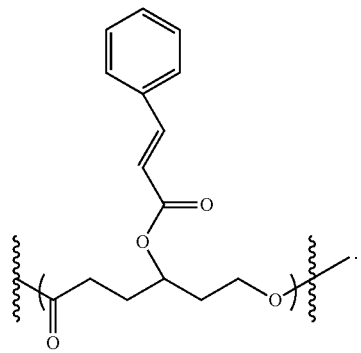

(V)

16. The polymer of claim 13, wherein the repeat unit of structural formula (IV) is represented by the following structural formula:

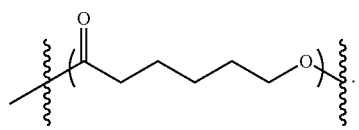

(VI)

17. The polymer of claim 14, comprising at least one repeat unit selected from the repeat unit of structural formula (V), and further at least one repeat unit of structural formula (VI).

18. A method of cross-linking a polymer, comprising:
irradiating a starting polymer comprising at least one repeat unit of structural formula (III) with actinic radiation

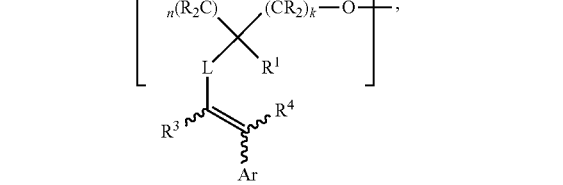

(III)

thereby producing a polymer having at least two cross-linked repeat units represented by structural formulas (VIII) or (VIIIA)

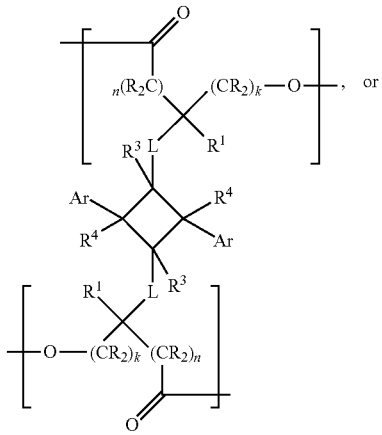

(VIII)

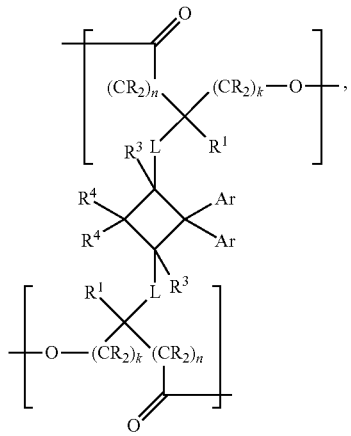

(VIIIA)

wherein:
Ar is for each occurrence independently an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group;

k and n are each independently zero or an integer between 1 and 6, provided that k+n≤14;

L for each occurrence independently is selected from —X—, —N(R$^2$)—, —C(X)—, —C(X)X—, —XC(X)—, —C(X)NR$^2$—, —NR$^2$C(X)—, —N(R$^2$)—S(O)$_{-m}$—, —S(O)$_m$—N(R$^2$)—;

each X is independently an O or an S;

m for each occurrence independently is 1 or 2;

R, R$^1$, R$^2$, R$^3$ and R$^4$ for each occurrence independently is selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkynyl group, C1-C12 alkoxy, or C1-C12 haloalkyl.

19. The method of claim 9, wherein the starting polymer further comprises at least one repeat unit of the following structural formula:

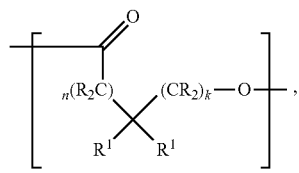
(IV)

wherein R¹ for each occurrence independently is as defined in claim 17.

20. The method of claim 19, wherein the starting polymer comprises from 1 to 99% by weight of the repeat units of structural formula (III).

21. The method of claim 20, wherein the starting polymer comprises from 20 to 50% by weight of the repeat units of structural formula (III).

22. The method of claim 20, wherein the starting polymer further comprises at least one initiator.

23. The method of claim 22, wherein the initiator is 2,2'-(ethane-1,2-diylbis(oxy))diethanol.

24. The method of claim 23, wherein R, R¹, R², R³ and R⁴ for each occurrence independently is selected from a hydrogen, a C1-C12 alkyl, a C3-C12 cycloalkyl, a C2-C12 alkenyl, a C3-C12 cycloalkenyl, a C3-C12 cycloalkynyl, a C2-C12 alkynyl, a (C6-C18)aryl(C6-C12)alkyl, or a (C6-C18)heteroaryl(C6-C12)alkyl.

25. The method of claim 24, wherein each L is independently selected from —X—, —C(X)—, —N(R²)—, —C(X)X—, —XC(X)—, —C(X)NR²—, —NR²C(X)—.

26. The method of claim 25, wherein R¹, R², R³ and R⁴ each is hydrogen.

27. The compound of claim 26, wherein k and n are each independently selected from 0 to 3.

28. The method of claim 27, wherein for each occurrence independently X is O.

29. The method of claim 28, wherein each Ar is independently a C6-C18 aryl.

30. The method of claim 29, wherein:
R for each occurrence independently is selected from a hydrogen, a C1-C12 alkyl, a C3-C12 cycloalkyl, a C2-C12 alkenyl, a (C6-C18)aryl(C6-C12)alkyl, or a (C6-C18)heteroaryl(C6-C12)alkyl; and
L for each occurrence independently is selected from —C(X)—, —C(O)O—, or —OC(O)—.

31. The compound of claim 30, wherein k and n are each from 0 to 2.

32. The method of claim 31, wherein the repeat unit of structural formula (III) is represented by the following structural formula:

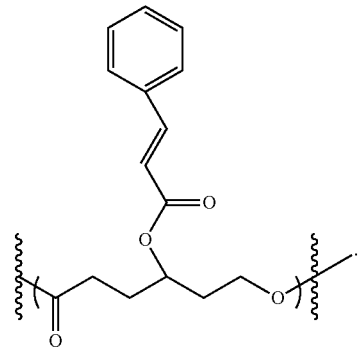
(V)

33. The method of claim 31, wherein the repeat unit of structural formula (III) is represented by the following structural formula:

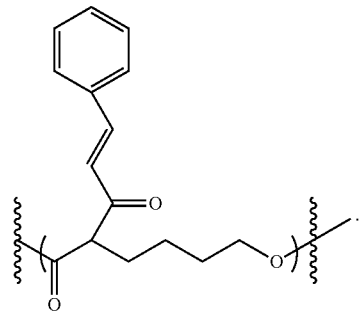
(X)

34. The method of claim 32, wherein the repeat unit of structural formula (IV) is represented by the following structural formula:

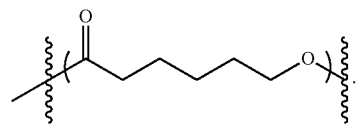
(VI)

35. The method of claim 34, wherein the starting polymer comprises at least one repeat unit selected from the repeat unit represented by structural formula (V) or structural formula (X), and at least one repeat unit of structural formula (VI).

36. A method of synthesis of a polymer having at least one subunit represented by the following structural formula

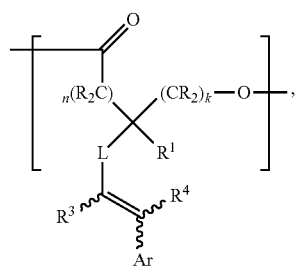
(III)

comprising:
reacting a compound of structural formula (I)

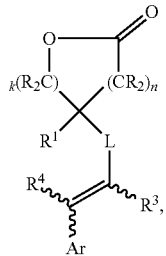
(I)

with a compound of structural formula (VII)

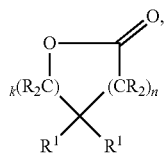
(VII)

thereby producing the polymer having at least one subunit of structural formula (III),
wherein:
Ar is an aryl or a heteroaryl, optionally substituted with one or more substituents selected from halogen, hydroxyl, C1-C12 alkyl, C2-C12 alkene, C2-C12 alkyne, C3-C12 cycloalkyl, C1-C12 haloalkyl, C1-C12 alkoxy, C6-C18 (hetero)aryloxy, C6-C18 (hetero)arylamino or a C6-C18 (hetero)aryl group;
k and n are each independently zero or an integer between 1 and 6, provided that k+n≤14;
L is selected from
—X—, —N(R$^2$)-, —C(X)X—, —XC(X)—, —C(X)NR$^2$-, —NR$^2$C(X)—, —N(R$^2$)-S(O)m-, —S(O)m-N(R$^2$)-;
each X is independently an O or an S;
m is 1 or 2;
R, R$^1$, R$^2$, R$^3$ and R$^4$ for each occurrence independently is selected from hydrogen, C1-C12 alkyl, C2-C12 alkene, C2-C12 alkyne, C3-C12 cycloalkyl or a C6-C18 (hetero)aryl group, wherein each C1-C12 alkyl, C2-C12 alkene, C2-C12 alkyne, C3-C12 cycloalkyl or a C6-C18 (hetero)aryl group is optionally substituted with one or more halogen, hydroxyl, C1-C12 alkyl, C2-C12 alkenyl, C2-C12 alkynyl group, C1-C12 alkoxy, or C1-C12 haloalkyl.

37. The method of claim 36, wherein from 1 to 99% by weight of the compound of structural formula (III) is reacted with from 1 to 99% by weight of the compound of structural formula (VII).

38. The method of claim 36, wherein from 20 to 50% by weight of the compound of structural formula (III) is reacted with from 50 to 80% by weight of the compound of structural formula (VII).

39. The method of claim 36, further comprising reacting the compounds of structural formulas (I) and (VII) with at least one initiator.

* * * * *